(12) United States Patent
Bowman et al.

(10) Patent No.: US 11,484,248 B2
(45) Date of Patent: Nov. 1, 2022

(54) SYSTEMS AND METHODS FOR ESTABLISHING THE STIFFNESS OF A ULNA BONE USING MECHANICAL RESPONSE TISSUE ANALYSIS

(71) Applicant: Ohio University, Athens, OH (US)

(72) Inventors: Lyn Bowman, Athens, OH (US); Joseph Oberhauser, Athens, OH (US)

(73) Assignee: Ohio University, Athens, OH (US)

( * ) Notice: Subject to any disclaimer, the term of this patent is extended or adjusted under 35 U.S.C. 154(b) by 390 days.

(21) Appl. No.: 16/753,013

(22) PCT Filed: Oct. 18, 2018

(86) PCT No.: PCT/US2018/056479
§ 371 (c)(1),
(2) Date: Apr. 2, 2020

(87) PCT Pub. No.: WO2019/079575
PCT Pub. Date: Apr. 25, 2019

(65) Prior Publication Data
US 2020/0245924 A1    Aug. 6, 2020

Related U.S. Application Data

(60) Provisional application No. 62/574,401, filed on Oct. 19, 2017.

(51) Int. Cl.
*A61B 5/00* (2006.01)
*G01N 3/08* (2006.01)
(Continued)

(52) U.S. Cl.
CPC .......... *A61B 5/4504* (2013.01); *A61B 5/0053* (2013.01); *A61B 5/704* (2013.01);
(Continued)

(58) Field of Classification Search
CPC ..... A61B 5/4504; A61B 5/0053; A61B 5/704; A61B 2560/04; G01N 3/08; G01N 3/32; G01N 3/40; G01N 2203/0218
(Continued)

(56) References Cited

U.S. PATENT DOCUMENTS

| 5,006,984 A | 4/1991 | Steele |
| 5,487,395 A | 1/1996 | Strowe |

(Continued)

FOREIGN PATENT DOCUMENTS

WO    2014169217 A3    10/2014

OTHER PUBLICATIONS

International Search Report and Written Opinion pertaining to International Application No. PCT/US2018/056479 dated Dec. 21, 2018, 11 pgs.

*Primary Examiner* — Octavia Davis Hollington
(74) *Attorney, Agent, or Firm* — Dinsmore & Shohl LLP

(57) ABSTRACT

Parametric model based computer implemented methods for determining the stiffness of a bone and systems for estimating the stiffness of a bone in vivo. The computer implemented methods include determining a complex compliance frequency response function Y(f) and an associated complex stiffness frequency response function H(f) and independently fitting a parametric mathematical model to Y(f) and to H(f). The systems include a device for measuring the stiffness of the bone in vivo and a data analyzer to determine a complex compliance frequency response function Y(f) and an associated complex stiffness frequency response function H(f).

20 Claims, 12 Drawing Sheets

(51) Int. Cl.
    *G01N 3/32*         (2006.01)
    *G01N 3/40*         (2006.01)

(52) U.S. Cl.
    CPC ................ *G01N 3/08* (2013.01); *G01N 3/32* (2013.01); *G01N 3/40* (2013.01); *A61B 2560/04* (2013.01); *G01N 2203/0218* (2013.01)

(58) Field of Classification Search
    USPC ........................................................ 600/562
    See application file for complete search history.

(56) References Cited

U.S. PATENT DOCUMENTS

| | | | |
|---|---|---|---|
| 5,836,876 A | 11/1998 | Dimarogonas | |
| 2008/0194952 A1* | 8/2008 | Luo ..................... | A61B 8/0875 |
| | | | 600/437 |
| 2016/0058365 A1 | 3/2016 | Bowman et al. | |
| 2017/0095195 A1 | 4/2017 | Hunter et al. | |
| 2017/0181688 A1* | 6/2017 | Coleman ............. | A61B 5/4504 |
| 2020/0146616 A1* | 5/2020 | Bowman .............. | A61B 5/4504 |
| 2021/0045636 A1* | 2/2021 | Bowman .............. | A61B 5/7282 |

* cited by examiner

SYSTEMS AND METHODS FOR ESTABLISHING THE STIFFNESS OF A ULNA BONE USING MECHANICAL RESPONSE TISSUE ANALYSIS

CROSS-REFERENCE TO RELATED APPLICATION APPLICATIONS

This application is a National Stage Entry under 35 U.S.C. 071 of International Patent Application No. PCT/US2018/056479, filed Oct. 18, 2018, which claims priority to U.S. Provisional Patent Application Ser. No. 62/574,401, filed Oct. 19, 2017, the contents of which are hereby incorporated by reference in their entireties.

FIELD

This application generally relates to in-vivo determination of bone stiffness. Specifically, this application relates to systems and methods for establishing the stiffness of an ulna using improvements to mechanical response tissue analysis (MRTA) known as cortical bone mechanics technology (CBMT) including rotational adjustment of the arm to optimally align the ulna and radius bones of the arm.

BACKGROUND

Bone health affects the overall health and quality of life of people around the world; for example, over 1.5 million older Americans suffer fractures due to weak bones each year. The bony skeleton provides support, mobility, and protection to the body, and serves as a storage area for essential minerals such as calcium, phosphorus and magnesium. Bone is a composite material made up of protein, minerals, and living bone cells. Collagen protein serves as the framework of the bone and provides resilience and ductility. The minerals, in the form of crystals dispersed around and between collagen fibers, stiffen the bone's protein structure.

There are two types of bone: cortical (compact) and cancellous (trabecular). Cortical bone is configured for support and protection and is arranged as densely packed parallel collagen fibrils organized in layers. This dense cortical bone is located, for example, in the shafts (diaphyses) of the long and short bones of the extremities. Cancellous (trabecular) bone is a porous type of bone located, for example, at the ends (epiphyses) of long bones and in the vertebrae. Cancellous bone provides strength without adding much weight, as it is configured to transfer stresses to the stronger, more massive cortical bone.

Bone is a living tissue that is constantly turning over and regenerating throughout its lifespan. Old bone is broken down (resorbed), creating a void, and new bone is formed in the void. Under normal conditions there is a continuous cyclic remodeling of bone, where osteoclasts remove old and micro damaged bone by acidification and proteolytic digestion, and osteoblasts secrete collagen and other specialized matrix proteins to synthesize new bone. Many hormones, including vitamin D, parathyroid hormone, calcitonin, estrogen, and testosterone, are involved in the regulation and complex interaction between the skeleton, intestine, and kidneys to maintain mineral homeostasis in the body (bones). Overall bone health largely relies on the proper balance of such hormones. Additionally, adequate nutrition and high impact physical activity are contributors to adequate bone health. During childhood and through the teenage years, normal healthy bones experience more bone formation than resorption. However, as humans age, increased bone resorption, decreased bone formation, or a combination of both, lead to a weakening of bones as the net result is less bone formation than resorption.

Further, bone diseases may disrupt normal bone functioning and can make bones weak. One common bone disease is osteoporosis. Osteoporosis is a skeletal disorder characterized by decreased bone strength predisposing to an increased risk of fracture. There are two types of osteoporosis: (1) Type 1 osteoporosis is characterized by a rapid loss of cancellous bone and a small loss of cortical bone in the hips, spine, and wrists of postmenopausal women; and (2) Type 2 (senile) osteoporosis affects both elderly men and women and, is characterized by a loss of cortical and cancellous bone in predominantly cortical bone sites, which is where a majority of non-vertebral fractures after the age of 60 occur in both men and women.

The strength of bone depends on the quality of the bone including the architecture, turnover, damage accumulation, and mineralization of the bone. Bone mineral density (BMD) describes the amount of mineral per area measured and is believed to account for only approximately 70% of bone strength. Current techniques used to diagnose osteoporosis and identify fracture risk focus primarily on measuring bone mineral density. One such technique of measuring BMD is Dual-energy X-ray absorptiometry (DXA). DXA noninvasively measures the transmission of x-rays with high and low energy photons through the body. A DXA measurement represents the sum of cortical and trabecular bone within the bone area scanned as part of the procedure. The results of a DXA scan are presented as a Z score and a T score, where the Z score is the number of standard deviations the measured result is from the mean for age and sex and the T score compares the measured BMD result with the average BMD of healthy young adults.

Other such techniques used to measure BMD include peripheral quantitative computed tomography (pQCT) and high resolution peripheral quantitative computed tomography (HRpQCT), in which 2-dimensional DXA images are made from many different angles around the body or limb and processed by a computer to create a 3-dimensional representation of a body part. These 3-dimensional measurements of bone density and structure can be used as inputs for finite element analyses of bone stiffness and strength.

However, such techniques of measuring BMD are limited in that they are not capable of providing direct insight into the mechanical properties of the bone. For example, changes in the mechanical properties of the bone can increase fracture risk while leaving bone mineral density intact, thus remaining undetected by such conventional screening methods.

Techniques for direct biomechanical testing of bone have also been developed. Direct biomechanical testing of bone is desired in that it provides information about mechanical integrity of bone. Currently, quasistatic mechanical testing (QMT) is the gold standard for directly measuring the strength of materials, including bone. QMT measures the force required to deform a bone at a very slow speed, and thereby at a very low strain rate, versus the associated displacement. QMT can be utilized in the performance of many differing types of mechanical tests such as, e.g., 3-point bending. To perform 3-point bending, or flexure tests, the specimen (bone) is supported at each end, and a force is applied at the midspan, where the sensitivity is greatest to the elastic modulus and other mechanical properties at that site. As the bone bends, fibers near the top surface undergo compressive forces and the fibers near the lower surface experience tensile forces.

Bone bending strength represents the maximum bending force a bone can bear before it breaks. Bone bending strength is measured with QMT as the peak force prior to fracture in a bending test, which occurs in the plastic region of the bone. The plastic region being the area under a force-displacement curve where permanent damage is accumulating within the bone, whereas the elastic region represents the area under a force-displacement curve where no permanent damage is being done and the bone will return to its original shape when the force is released. Bone bending stiffness ($K_B$) is the resistance of a bone to bending and can be measured, for example, by QMT by applying increasing forces to the bone and measuring the slope of the force displacement curve in the elastic region of the bone.

QMT is thus limited in that it can only be used on excised bones and bone samples. More particularly, although QMT can make direct measurements of bone bending strength and stiffness, its use in vivo is limited in that: (1) QMT is not able to differentiate between skin compression and bone bending, which may result in an inaccurate estimation of bone displacement; and (2) measurement of bone strength by QMT requires fracturing of the bone. However, it is well known that measurements of bone bending stiffness accurately predict measurements of bone bending strength. Thus, the inventors recognize a need for improved methods and systems for assessing the stiffness of bone in vivo.

SUMMARY

It is against this background that the present disclosure provides methods for determining the stiffness of a bone and systems for estimating the stiffness of a bone in vivo.

In various embodiments, a parametric model based computer implemented method for determining the stiffness of a human ulna bone is disclosed. The computer implemented method includes (1) supporting an arm comprising the ulna bone and a radius bone on a cradle, the cradle providing controllable positioning and rotation of the arm with the styloid process of the radius bone resting on the cradle; (2) applying a superposition of static and oscillatory forces (F) over a range of frequencies (f) to a region of a skin-bone complex comprising the ulna, the radius, and the overlying muscle and skin thereby exciting oscillatory accelerations (a) over the range of frequencies (f) of the skin-bone complex; (3) receiving measurement data of the oscillatory forces (F) as functions of time F(t) and obtaining the resulting oscillatory acceleration data (a) as functions of time a(t) with a data receiver communicatively coupled to a controller including a processor and a storage medium containing computer readable and executable instructions; (4) adjusting a rotational position of the arm in the cradle such that a distal end of the radius bone is controllably rotated under the ulna bone; (5) repeating step (2)-(4), such that the static and oscillatory forces (F) in step (2) are applied to ta rotationally shifted region of the skin-bone complex, thereby obtaining a parameter set for the rotationally shifted region of the skin-bone complex; (6) repeating step (5) until an optimized parameter set is determined based on the measure of conformity; and (7) determining the stiffness of the bone from ($K_B$) values of the optimized parameter set. When executed by the processor, the computer readable and executable instructions cause the controller to automatically: (i) transform a(t) and F(t) to functions of frequency, a(f) and F(f), (ii) reduce a(f) and F(f) to accelerance frequency response function data A(f), (iii) determine, a complex compliance frequency response function, Y(f) and associated complex stiffness frequency response function H(f), (iv) fit a parametric mathematical model to Y(f), by iteratively convergent operations, to obtain a first complete and fully converged set of parameters of the parametric mathematical model, including the stiffness of the bone ($K_B$), (v) independently fit the parametric mathematical model to H(f), by iteratively convergent operations, to obtain a second complete and fully converged set of parameters of the parametric mathematical model, including the stiffness of the bone ($K_B$), (vi) after fitting, determine discrepancies between each parameter of the first complete and fully converged set of parameters and each corresponding parameter of the second complete and fully converged set of parameters as a measure of conformity thereof to the parametric mathematical model, and (vii) save the measure of conformity, the first complete and fully converged set of parameters, and the second complete and fully converged set of parameters as a parameter set for the measured region of the skin-bone complex.

In other embodiments, a system for estimating the stiffness of an ulna bone in vivo is disclosed. The system includes a device for measuring the stiffness of the ulna bone in vivo and a data analyzer. The device for measuring the stiffness of the ulna bone in vivo includes a bone support, a mechanical force applicator, and a frequency response recorder, in which the bone support is configured to position and support an arm comprising the ulna bone and a radius bone in an orientation and position for measurement and comprises a cradle, the cradle providing controllable positioning and rotation of the arm with the styloid process of the radius bone resting on the cradle. The mechanical force applicator includes a force transducer and a force probe and is configured to apply a superposition of static and oscillatory forces (F) over a range of frequencies (f) to a region of the skin-bone complex comprising the ulna, the radius, and the overlying muscle and skin, wherein the oscillatory forces (F) excite oscillatory accelerations (a) of the skin-bone complex. The frequency response recorder is configured to measure and transmit to the data analyzer the oscillatory forces as functions of time F(t) and the oscillatory accelerations as functions of time a(t). The data analyzer is communicatively coupled to the force transducer and frequency response recorder. The data analyzer includes a storage medium containing computer readable and executable instructions for collecting the transmitted oscillatory forces as functions of time F(t) and oscillatory accelerations as functions of time a(t) of the skin-bone complex, the storage medium storing a parametric mathematical model of the skin-bone complex. The data analyzer also includes a processor for executing the instructions to transform a(t) and F(t) to functions of frequency, a(f) and F(f), to reduce a(f) and F(f) to accelerance frequency response data A(f), to determine a complex compliance frequency response function Y(f) and associated complex stiffness frequency response function H(f), to fit the parametric mathematical model to Y(f) to obtain a first complete and fully converged set of parameters of the parametric mathematical model, including the stiffness of the bone ($K_B$), to independently fit the parametric mathematical model to H(f) to obtain a second complete and fully converged set of parameters of the parametric mathematical model, including the stiffness of the bone ($K_B$), and to determine the discrepancies between the first complete and fully converged set of parameters and the second complete and fully converged set of parameters as a measure of conformity thereof to the parametric mathematical model.

BRIEF DESCRIPTION OF THE DRAWINGS

A more complete appreciation of the invention and the many embodiments thereof will be readily obtained as the same becomes better understood by reference to the following detailed description when considered in connection with the accompanying drawings, wherein.

Figure 1:
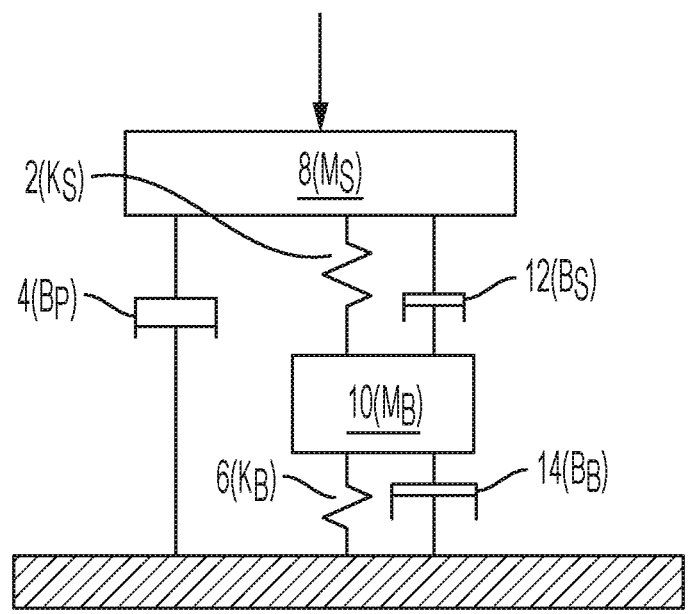
FIG. 1 depicts a schematic of a model of a skin-bone complex.

The provided drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several embodiments of the invention, and together with the description serve to explain the principles of the invention; it being understood, however, that the invention is not limited to the precise arrangements shown.

DETAILED DESCRIPTION OF THE INVENTION

Specific embodiments of the present application will now be described. The invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art. The terminology used in the description herein is for describing particular embodiments only and is not intended to be limiting. As used in the specification and appended claims, the singular forms "a," "an," and "the" are intended to include the plural forms as well, unless the context clearly indicates otherwise.

Recitations of "at least one" component, element, etc. in the present disclosure and appended claims should not be used to create an inference that the alternative use of the articles "a" or "an" should be limited to a single component, element, etc.

In the present disclosure and appended claims, recitations of a component being "configured" to embody a particular property, or function in a particular manner, are structural recitations, as opposed to recitations of intended use. More specifically, references to the manner in which a component is "configured" denotes an existing physical condition of the component and, as such, is to be taken as a definite recitation of the structural characteristics of the component.

As used in the present disclosure and appended claims, terms like "preferably," "commonly," and "typically" are not utilized to limit the scope of the claims or to imply that certain features are critical, essential, or even important to the structure or function of the claimed embodiments. Rather, these terms are merely intended to identify particular aspects of an embodiment of the present disclosure or to emphasize alternative or additional features that may or may not be utilized in a particular embodiment of the present disclosure.

The terms "substantially" and "approximately," as used in the present disclosure and appended claims, represent the inherent degree of uncertainty that may be attributed to any quantitative comparison, value, measurement, or other representation. Such terms are also utilized to represent the degree by which a quantitative representation may vary from a stated reference without resulting in a change in the basic function of the subject matter at issue.

Unless otherwise indicated, all numbers expressing quantities, properties, conditions, and so forth as used in the specification and claims are to be understood as being modified in all instances by the term "about." Additionally, the disclosure of any ranges in the specification and claims are to be understood as including the range itself and also anything subsumed therein, as well as endpoints. Notwithstanding that numerical ranges and parameters setting forth the broad scope of the disclosure are approximations, the numerical values set forth in the specific examples are reported as precisely as possible. Any numerical values, however, inherently contain certain errors necessarily resulting from error found in their respective measurements.

"Automatically" includes the use of a machine to conduct a particular action. The process by which data is extracted, organized and stored is a data-driven and largely automatic process and may utilize a computer network (e.g., wide area network, such as the internet, a local area network, a mobile communications network, a public service telephone network, and/or any other network) and may be configured to electronically connect a user computing device (e.g., a PC) and a server computing device (e.g., cloud, mainframe, or other server device).

"Calculate" includes automatically determining or ascertaining a result.

"Computer" includes a machine (e.g., desktop, laptop, tablet, smartphone, television, server, as well as other current or future computer instantiations) containing a computer processor that has been specially configured with a set of computer executable instructions. References to "at least one" computer are intended to encompass both autonomous systems and sub-systems as well as situations where a given functionality might be divided across multiple machines (e.g. parallel processing) for efficiency or other purposes.

"Data Receiver" as used herein includes any component configured to receive data.

"Exemplary" as used herein means giving an example; serving as an illustration or example of something.

"GUI" or "Graphical User Interface" includes a user interface displayed on a visual subsystem (e.g., desktop monitor, tablet/phone screen, interactive television screen, etc.) by which users interact with electronic devices via images (e.g., lists, hyperlinks, panels, etc.).

"Parametric Mathematical Model" as used herein includes any mathematical model which can be described using a finite number of parameters.

A "Processor" may include any processing component configured to receive and execute instructions (such as from the data storage component and/or memory component). Network interface hardware may include any wired/wireless hardware generally known to those of skill in the art for communicating with other networks and/or devices.

"Root Mean Square," also known as the quadratic mean and abbreviated RMS, as used herein is a statistical measure of the magnitude of a varying quantity and is calculated as the square root of the arithmetic mean (average) of the squares of the original values.

A "Skin-Bone Complex" as used herein is bone and the overlying soft tissue including skin and muscle.

A "Server" may be specially configured or configured as a general purpose computer with the requisite hardware, software, and/or firmware. A server may include a processor, input/output hardware, network interface hardware, a data storage component (which stores data and/or metadata) and a memory component configured as volatile or non-volatile memory including RAM (e.g., SRAM, DRAM, and/or other types of random access memory), flash memory, registers, compact discs (CDs), digital versatile discs (DVD), and/or other types of storage components. A memory component may also include operating logic that, when executed, facilitates the operations described herein. An administrative computing device may also be employed to facilitate manual corrections to the metadata.

"Viscoelastic Material" as used herein includes material that has both damping and elastic properties.

In embodiments, a parametric model based computer implemented method for determining the stiffness of a bone is disclosed. Stiffness, as used herein, is the mechanical property measuring the resistance offered by an elastic body to deformation. It can be represented by $F/\delta$, wherein F is the force applied to the body and $\delta$ is the displacement produced by the force. In some embodiments, the computer implemented method utilizes improvements to mechanical response tissue analysis (MRTA) known as cortical bone mechanics technology (CBMT). In one or more embodiments, Mechanical Response Tissue Analysis and improved CBMT involves a two-step technique for measuring the mechanical properties (i.e., mass, stiffness and damping) of long bones, such as the ulna in the human arm. While the techniques of MRTA and improved CBMT may be applicable to multiple bones in the body, for purposes of conveniently describing certain embodiments thereof, reference will be made to the ulna. The first step of MRTA and improved CBMT generally involves the collection of data in the form of a complex acceleration frequency response function, A(f). The second step of MRTA and improved CBMT generally involves the analysis of this complex acceleration frequency response function, A(f), by fitting A(f) to a parametric mathematical model of the skin-bone complex to estimate the values of mechanical properties thereof. The parametric mathematical model takes the form of a complex rational polynomial. The purpose of the disclosed embodiments is to facilitate the collection of a complex acceleration frequency response function, A(f) that conforms well to the parametric mathematical model.

To facilitate collection of the complex acceleration frequency response function, A(f), an arm comprising an ulna bone, a radius bone and surrounding soft tissue is supported on a cradle. The cradle provides controllable positioning and rotation of the arm. In embodiments, the styloid process of the radius bone rests on the cradle and the cradle may be controllably adjusted to achieve rotation of the radius bone under the ulna bone to achieve proper positioning of the arm for optimized complex acceleration frequency response function collection. Because the ulna bone articulates with the humerus bone via a hinge joint, the ulna cannot rotate on its long axis. Instead, rotation of the wrist is achieved by rolling the distal radius bone around the distal ulna bone. Details regarding the cradle and controllable adjustment thereof are provided subsequently in this disclosure.

Figure 2:
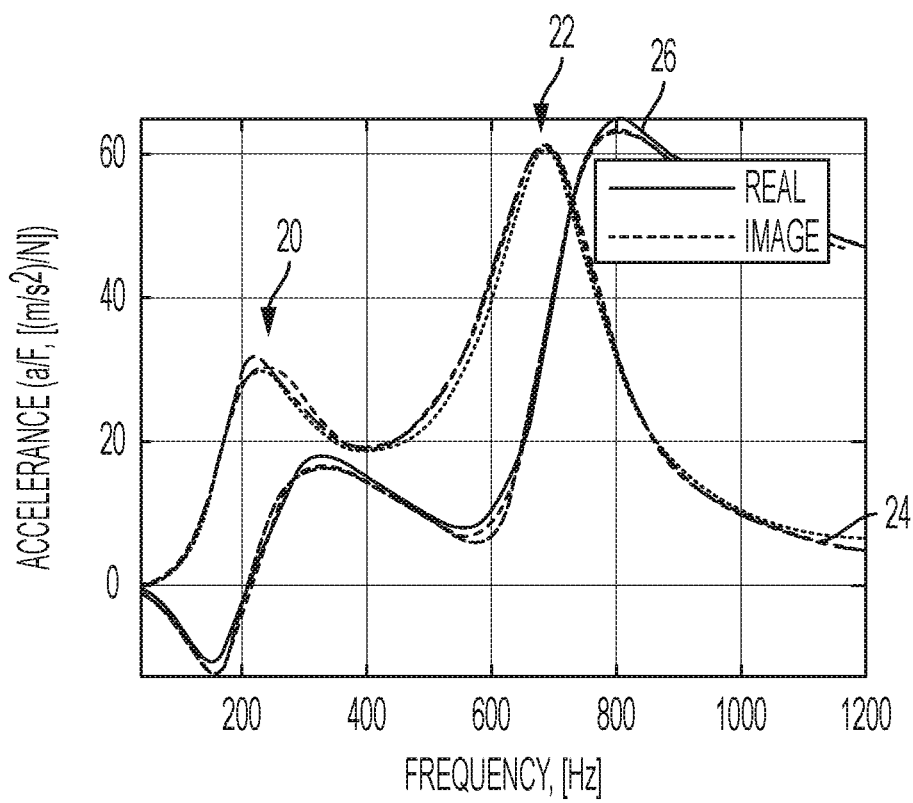
FIG. 2 depicts accelerance frequency response function data A(f) and the parametric mathematical model best fit.

With reference to FIG. 2, the first step of MRTA and improved CBMT involves collecting data in the form of a complex acceleration frequency response function, A(f), of a skin-bone complex. The skin-bone complex is bone and the overlying soft tissue including skin and muscle such as an arm comprising an ulna, a radius, and the overlying skin and muscles. In some embodiments, the complex acceleration frequency response function, A(f), data are collected by: (1) positioning a force probe on the skin overlying the bone, (2) applying both (i) a static force and (ii) oscillatory forces (F), (3) varying the frequency of the oscillatory forces (F) over a sub-range of the auditory frequency range, (4) measuring (i) the force applied through the force probe to the skin and (ii) the resulting acceleration of the force probe on the skin to obtain an oscillatory acceleration (a) of the skin-bone complex, and (5) calculating acceleration (i.e., acceleration divided by force) as a complex function of frequency, i.e., the complex acceleration frequency response function, A(f).

A "complex" function of frequency is one that records both (1) the magnitude of the oscillatory acceleration (a) that occurs in response to the applied oscillatory forces (F) relative to the magnitude of the oscillatory forces (F), and (2) the phase delay between the peak of the oscillatory forces (F) and the peak of the oscillatory acceleration (a). Mathematically equivalently, the magnitude and phase delay of a "complex" function of frequency may be expressed and recorded as a real part 26 and an imaginary part 24, wherein the real part 26 is equal to the magnitude multiplied by the cosine of the phase delay, and the imaginary part 24 is equal to the magnitude multiplied by the sine of the phase delay.

In some embodiments, the second step in MRTA and improved CBMT involves analysis of the complex accelerance frequency response function, A(f), to determine the mechanical properties of the bone. Such analysis includes fitting the complex accelerance frequency response function, A(f), to the parametric mathematical model. The parametric mathematical model represents the mechanical behavior of the skin-bone complex. Referring to FIG. 1, in one or more embodiments, the parametric mathematical model includes 7 parameters and accounts for the mass, stiffness, and damping of the skin and bone as well as parallel damping of soft tissues. Specifically, the 7-parameter model accounts for mass of the skin 8 ($M_S$), compressive stiffness of the skin 2 ($K_S$), damping coefficient of the skin 12 ($B_S$), mass of the bone 10 ($M_B$), transverse bending stiffness of the bone 6 ($K_B$), damping coefficient of the bone 14 ($B_B$), and damping coefficient of the surrounding soft tissue 4 ($B_P$). These parameters may alternatively be referenced using lowercase letters, e.g. ($m_s$), ($k_s$), ($b_s$), ($m_b$), ($k_b$), ($b_b$), and ($b_p$). While the present disclosure is applicable to numerous parametric mathematical models, for purposes of conveniently describing certain embodiments thereof, reference will be made to the 7-parameter model. However, one of skill in the art will recognize that reference to the 7-parameter model is not intended to be limiting and that the methods and systems disclosed herein may be applicable to alternate parametric mathematical models.

Integrating A(f) twice with respect to frequency yields a complex compliance frequency response function, Y(f)=x(f)/F(f) in which "x" is displacement. Inverting Y(f) yields the associated complex stiffness frequency response function, H(f)=F(f)/x(f).

The differential equations of motion representing the parametric mathematical model with 7-parameters are:

$$F - K_S(x_S - x_B) - B_S\left(\frac{dx_S}{dt} - \frac{dx_B}{dt}\right) - B_P\frac{dx_S}{dt} = M_S\frac{d^2x_S}{dt^2}$$

$$K_S(x_S - x_B) - K_B x_B + B_S\left(\frac{dx_S}{dt} - \frac{dx_B}{dt}\right) - B_B\frac{dx_B}{dt} = M_B\frac{d^2x_B}{dt^2}$$

As H(f)=Real{H(f)}+j Imag{H(f)}, wherein $\omega=2\pi f$, H(f) can be determined in terms of things which are known and measurable. Specifically, $$\text{Real}\{H(\omega)\} = \frac{M_S[(C_0 - \omega^2)(\omega^4 - A_2\omega^2 + A_0) - C_1\omega(A_3\omega^3 - A_1\omega)]}{(C_0 - \omega^2)^2 + (C_1\omega)^2}$$

$$\text{Imag}\{H(\omega)\} = \frac{M_S[C_1\omega(\omega^4 - A_2\omega^2 + A_0) + (C_0 - \omega^2)(A_3\omega^3 - A_1\omega)]}{(C_0 - \omega^2)^2 + (C_1\omega)^2}$$

wherein, $$A_0 = \frac{K_S K_B}{M_S M_B}$$

$$A_1 = \frac{[K_B(B_S + B_P) + K_S(B_B + B_P)]}{M_S M_B}$$

$$A_2 = \frac{(K_S + K_B)}{M_B} + \frac{K_S}{M_S} + \frac{[B_S(B_B + B_P) + B_B B_P]}{M_S M_B}$$

$$A_3 = \frac{(B_S + B_P)}{M_B} + \frac{(B_S + B_P)}{M_S}$$

$$C_1 = \frac{(B_S + B_B)}{M_B}$$

$$C_0 = \frac{(K_S + K_B)}{M_B}$$

Inverting the associated complex stiffness frequency response function, H(f), generates complex compliance frequency response function, Y(f).

Utilizing basic algebraic manipulation, the values for each of the 7 parameters can be determined from the fitted regression coefficients, $A_0$, $A_1$, $A_2$, $A_3$, $C_1$, and $C_0$. In embodiments, the determination of each of the 7 parameters is independently made from Y(f) and from H(f).

In theory, for data conforming perfectly to the 7-parameter model, fitting the 7-parameter model to Y(f) and H(f) should yield exactly the same values for each of the 7 parameters. However, in practice the values of the 7 parameters vary between those obtained from Y(f) and those obtained from H(f). Therefore, the extent to which these values of the 7 parameters differ from one another is a measure of the extent to which the data do not conform to the 7-parameter model.

In embodiments, the static force applied to the skin overlying the bone serves at least two functions. As approximated by the 7-parameter model of the skin-bone complex of the forearm, the skin-bone complex has two resonances, the properties of which are determined primarily, but not entirely, by the bone in one case and by the skin and other soft tissue between the surface of the skin and the bone in the other case. The first function of the static load is to exceed the amplitude of the oscillatory forces (F), so that the force probe does not separate from the arm on every negative phase of the oscillatory forces (F). The second function of the static load is to compress the soft tissue overlying the ulna, squeezing tissue fluid out from between the surface of the skin and the underlying bone, thereby increasing the stiffness and reducing the mass of this tissue. Because the resonant frequency of a mechanical system is proportional to the square root of the system's effective stiffness divided by its effective mass, increasing the static load increases the frequency of the resonance associated with the skin, separating it from the resonance associated with the ulna, and thereby improving the ability to more accurately estimate the mechanical properties of the bone and skin. The magnitude of the static load that optimizes these estimates varies with individual differences in the amount of soft tissue between the surface of the skin and the underlying ulna, and is best determined by iteratively collecting and analyzing data, and adjusting the static load in such a manner as to maximize conformity of the data to the 7-parameter model. In various embodiments, the static load varies between approximately 3 N and approximately 30 N. Static loads lower than approximately 3 N are generally insufficient, even in lean patients and static loads greater than approximately 30 N are painful, even in obese or muscular people. In other embodiments the range of static loads varies within a subrange of approximately 3 N and approximately 30 N, such as between approximately 3 N and approximately 25 N, between approximately 5 N and approximately 30 N or, between approximately 10 N and approximately 20 N.

In embodiments of a parametric model based computer implemented method for determining the stiffness of a bone, the method initially comprises applying a superposition of static and oscillatory forces (F) over a range of frequencies (f), i.e. vibrations, to a region of the skin-bone complex of a bone of interest, e.g., the ulna. The oscillatory forces (F) applied to the skin-bone complex induce corresponding oscillatory accelerations (a) over the range of frequencies (f) of the skin-bone complex. Further, a data receiver receives measurement of the oscillatory forces as functions of time F(t) and the resulting oscillatory accelerations (a) as functions of time a(t). The data receiver is communicatively coupled to a controller. Communicatively coupled means electrically, signally, wirelessly, wired, optically, or similarly connected. The controller comprises a processor and a storage medium containing computer readable and executable instructions which, when executed by the processor, cause the controller to automatically execute a series of analysis steps to determine the stiffness of the bone based on the measured oscillatory forces as functions of time F(t) and the resulting oscillatory accelerations as functions of time a(t).

Figure 3:
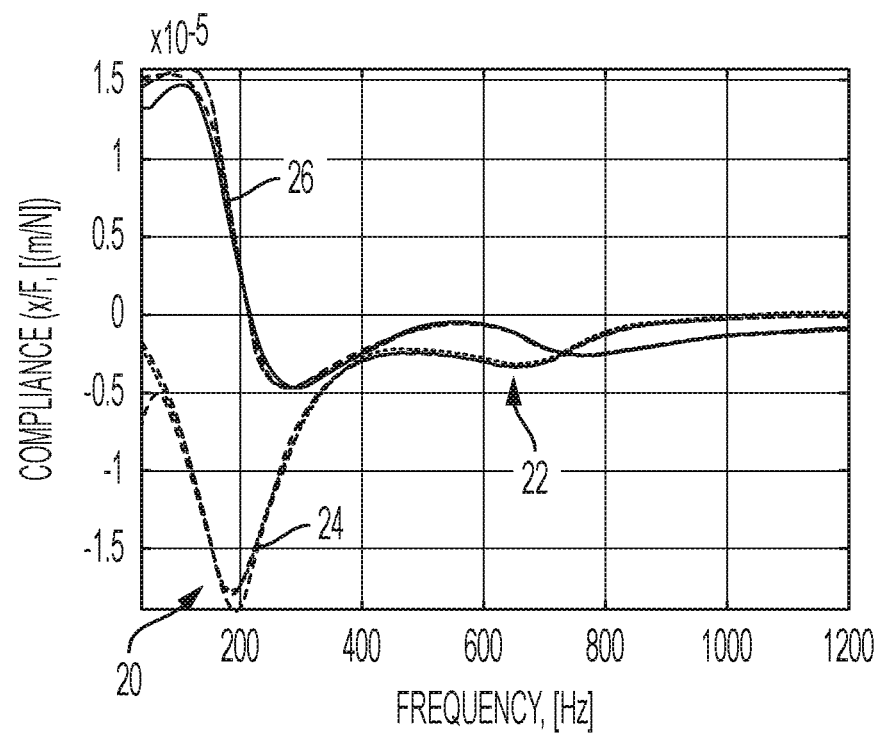
FIG. 3 depicts complex compliance frequency response function Y(f) and the parametric mathematical model best fit.
Figure 4:
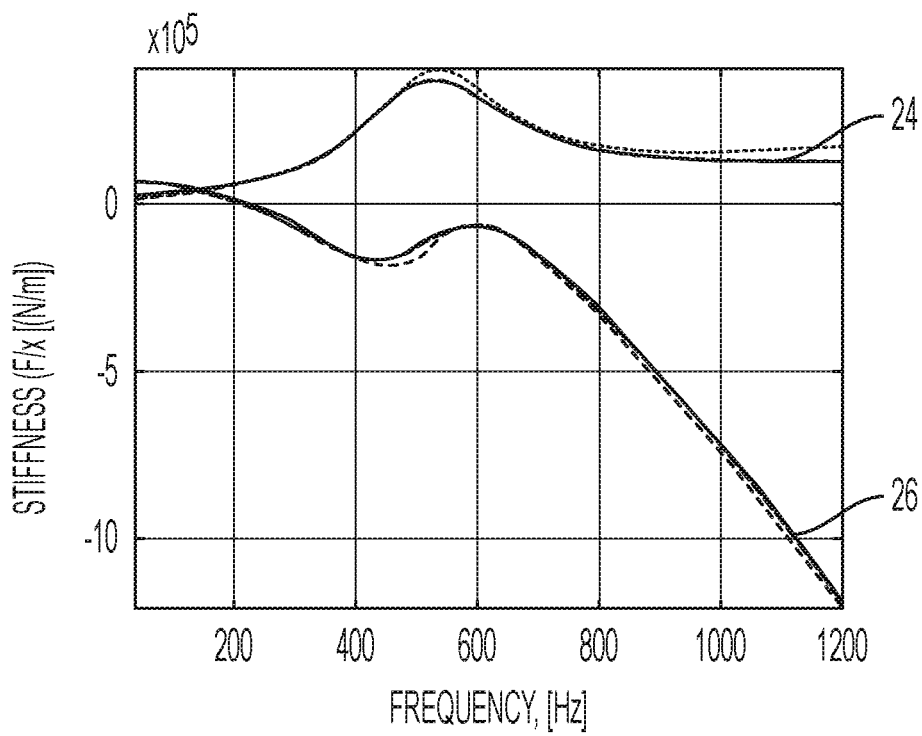
FIG. 4 depicts complex stiffness frequency response function H(f) and the parametric mathematical model best fit.

With reference to FIGS. 3 and 4, the controller, in accordance with the executable instructions on the storage medium containing computer readable and executable instructions, automatically determines the oscillatory acceleration (a) and oscillatory forces (F) as functions of frequency, a(f) and F(f) respectively by performing Fourier transformations to convert a(t) and F(t) to a(f) and F(f) respectively. Additionally, the controller automatically determines the complex compliance frequency response function, Y(f) and the associated complex stiffness frequency response function H(f). In embodiments Y(f) and H(f) are determined by reducing a(f) and F(f) to the complex accelerance frequency response function A(f) and integrating A(f) twice in accordance with the mathematical manipulation previously discussed. Additionally, the controller automatically fits a parametric mathematical model to Y(f) to obtain a first complete and fully converged set of parameters of the parametric mathematical model, including the stiffness of the bone ($K_B$), as well as fits the parametric mathematical model to H(f) to obtain a second complete and fully converged set of parameters of the parametric mathematical model, including the stiffness of the bone ($K_B$). The parametric mathematical model may also be as previously discussed. The controller further automatically determines discrepancies between the first complete and fully converged set of parameters and the second complete and fully converged set of parameters as a measure of conformity thereof to the parametric mathematical model and saves the measure of conformity, the first complete and fully converged set of parameters, and the second complete and fully converged set of parameters as a parameter set.

As shown in FIGS. 2, 3, and 4, when the measure of conformity indicates a good fit, the fit parametric mathematical model conforms to the collected data closely. Specifically, between approximately 150 Hz and 725 Hz, the fit parametric mathematical model can be seen graphically overlaid over the empirical A(f), Y(f), and H(f) in FIG. 2, FIG. 3, and FIG. 4 respectively. Additionally, both the imaginary part 24 and the real part 26 of each of A(f), Y(f), and H(f) are shown.

In various embodiments the saving of the measure of conformity, the first complete and fully converged set of parameters, and the second complete and fully converged set of parameters as a parameter set is completed using the storage medium. In some embodiments every parameter set generated is saved and retained in the storage medium. In further embodiments, only a predetermined number of parameter sets are retained in the storage medium and as new parameter sets are generated the oldest parameter sets are deleted and/or written over. In still further embodiments, in lieu of, or in addition to, saving the parameter sets to the storage medium the parameter sets are physically printed such that hard copies of the measure of conformity, the first complete and fully converged set of parameters, and the second complete and fully converged set of parameters in each parameter set are generated. In yet further embodiments, the parameter sets are saved on a storage medium located in a server external to the system.

In other embodiments the parameter set also includes a record of Y(f), H(f), or Y(f) and H(f). Retaining the raw data representing Y(f) and/or H(f) allows repeated or alternative analysis to be performed at a later time.

Further, in an effort to obtain an optimized parameter set, the rotational position of the arm is adjusted such that the distal end of the radius bone is controllably rotated under the ulna bone before repeating application of the static and oscillatory forces (F) to the skin-bone complex. The data receiver receives measurement of the oscillatory forces as functions of time F(t) and the resulting oscillatory accelerations (a) as functions of time a(t). for the repositioned arm. The controller, in accordance with the executable instructions on the storage medium containing computer readable and executable instructions, automatically determines the oscillatory acceleration (a) and oscillatory forces (F) as functions of frequency, a(f) and F(f) respectively by performing Fourier transformations to convert a(t) and F(t) to a(f) and F(f) respectively for the rotatably repositioned arm. Additionally, the controller automatically determines the complex compliance frequency response function, Y(f) and the associated complex stiffness frequency response function H(f) for the rotatably repositioned arm. In embodiments Y(f) and H(f) are determined by reducing a(f) and F(f) to the complex accelerance frequency response function A(f) and integrating A(f) twice in accordance with the mathematical manipulation previously discussed. Additionally, the controller automatically fits the parametric mathematical model once again to the Y(f) to obtain a new iteration of the first complete and fully converged set of parameters of the parametric mathematical model, including the stiffness of the bone ($K_B$), as well as fits the parametric mathematical model to H(f) to obtain a new iteration of the second complete and fully converged set of parameters of the parametric mathematical model, including the stiffness of the bone ($K_B$). The controller further automatically determines discrepancies between the new iterations of the first complete and fully converged set of parameters and the second complete and fully converged set of parameters as a measure of conformity thereof to the parametric mathematical model and saves the measure of conformity, the first complete and fully converged set of parameters, and the second complete and fully converged set of parameters as a parameter set. Repetition of collection of the oscillatory forces (F) and the resulting oscillatory accelerations (a) for sequentially rotatably repositioned orientations of the arm and analysis of the collected oscillatory forces (F) and oscillatory accelerations (a) to determine parameters of the parametric mathematical model is continued until the optimized parameter set is determined.

In various embodiments the static force applied to the skin-bone complex is adjusted for some or all repetitions of collection of the oscillatory forces (F) and the resulting oscillatory accelerations (a) for the rotatably repositioned arm.

Figure 5A:
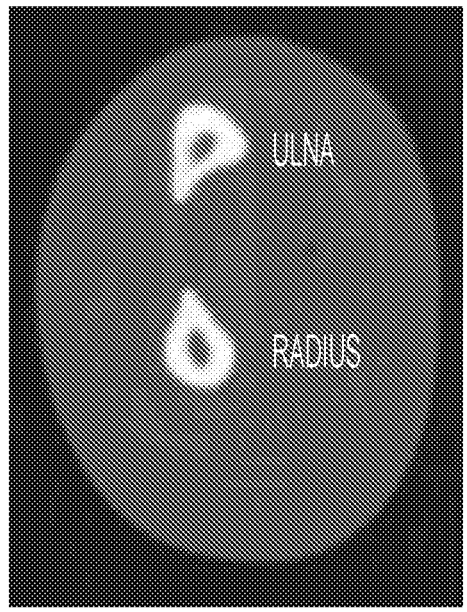
FIG. 5A depicts a cross-sectional CT (computer tomography) image of an ulna and radius midshaft.
Figure 5B:
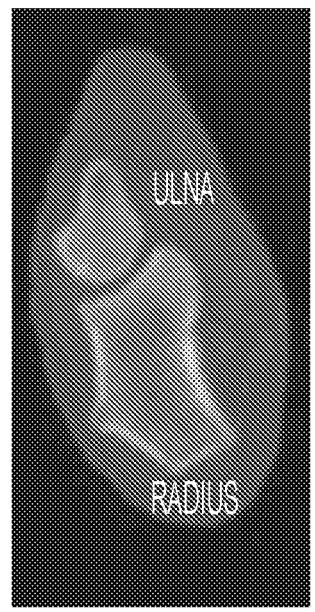
FIG. 5B depicts a cross-sectional CT image at the distal end of the ulna and radius in FIG. 5A with an unstable base of support provided by the radius at the distal end.
Figure 6A:
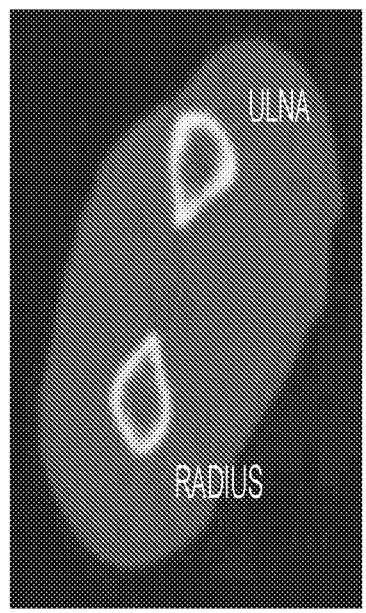
FIG. 6A depicts a cross-sectional CT image of an ulna and radius midshaft.
Figure 6B:
FIG. 6B depicts a cross-sectional CT image at the distal end of the ulna and radius in FIG. 6A with a stable base of support provided by the radius at the distal end.
Figures 7A, 7B:
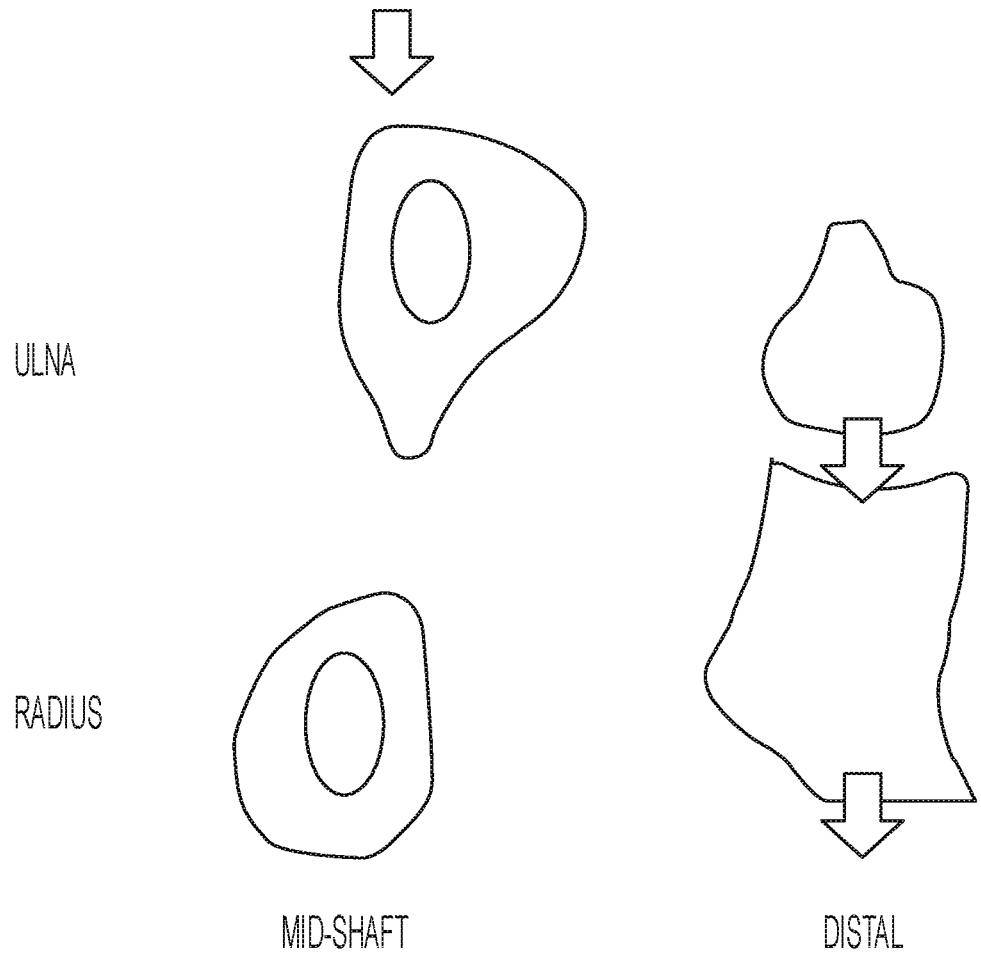
FIG. 7A depicts a schematic of a cross-section of an ulna and radius midshaft with a stable base of support provided by the radius at the distal end.
FIG. 7B depicts a schematic of a cross-section of the distal end of the ulna and radius in FIG. 7A with a stable base of support provided by the radius at the distal end.

The optimized parameter set is achieved by adjusting the rotational position of the arm such that the distal end of the radius bone is controllably rotated under the ulna bone because appropriate rotational positioning achieves maximum stability during testing. With reference to FIGS. 5A, 5B, 6A, 6B, 7A, and 7B, the maximum ulnar stability based on the rotational orientation of the ulna and radius is illustrated. FIGS. 5A-6B illustrate CT (computer tomography) images of a radius and an ulna in differing rotational orientations. Specifically, FIGS. 5A and 5B provide imaging for an orientation where the ulna is directly above the radius at the midshaft. However, at the distal end, where the arm is supported for MRTA and improved CBMT testing, the ulna bone is not in alignment with the radius and the radius is askew such that an unstable base of support is provided. Conversely, FIGS. 6A and 6B provide imaging for an orientation where the ulna bone is directly above the radius bone at the distal end, thereby providing a stable base of support. With reference to FIGS. 7A and 7B, the stable base of support and passage of force through the ulna and radius complex is illustrated graphically. At the midshaft, a downward load is applied to the ulna and illustrated with the downward arrow. This load is conveyed along the length of the ulna in both directions. At the distal end, half of this applied load passes from the ulna through the underlying radius bone to the base of support below as illustrated in FIG. 7B.

However, in practice MRTA and improved CBMT operators do not have access to cross-section CT images of the forearm to guide their rotation of the wrist into the desired stable orientation. Due to the inability to obtain real-time cross-section CT images or visualize the ulna and radius during MRTA and improved CBMT testing with skin and muscle blocking visualization, the operator during MRTA and improved CBMT testing is unable to immediately determine if the ulna and radius are in the most stable orientation. Controlled rotation of the ulna and radius and repeated data collection allows the optimum orientation to be iteratively achieved and determined based on the collected data.

In various embodiments one or more layers of a viscoelastic material is applied over the skin-bone complex. In other embodiments one or more layers of a viscoelastic material is applied under the skin-bone complex between the skin-bone complex and the structure upon which the skin-bone complex rests. In still other embodiments one or more layers of a viscoelastic material is applied both over the skin-bone complex and between the skin-bone complex and the structure upon which the skin-bone complex rests.

In an embodiment, the optimized parameter set is determined based on the measure of conformity. If, when the superposition of static and oscillatory forces (F) over a range of frequencies (f) are applied to a the skin-bone complex in a rotatably repositioned orientation the measure of conformity of the first complete and fully converged set of parameters and the second complete and fully converged set of parameters is improved, the first complete and fully converged set of parameters and the second complete and fully converged set of parameters of the rotated orientation are believed to represent an improved representation of the true parameters of the bone over the previous sets of parameters. The repetition of collection of the oscillatory forces (F) and the resulting oscillatory accelerations (a) for rotatably repositioned orientations of the arm and analysis of the collected oscillatory forces (F) and oscillatory accelerations (a) to determine parameters of the parametric mathematical model is continued until the measure of conformity is worsened. The worsening of the measure of conformity indicates the rotation has proceeded past the ideal orientation of the ulna bone and radius bone for data collection and the optimized parameter set is the immediately previously collected first complete and fully converged set of parameters and second complete and fully converged set of parameters. For example, the superposition of static and oscillatory forces (F) over a range of frequencies (f) may be initially applied to a region of the skin-bone complex after incremental rotation of the arm in a first direction with respect to its long axis, then the static and oscillatory forces (F) over a range of frequencies (f) are applied to a region of the skin-bone complex after further incremental rotation of the arm in the first direction, then the static and oscillatory forces (F) over a range of frequencies (f) are applied to a region of the skin-bone complex after incremental rotation of the arm yet further in the first direction. The measure of conformity improves upon each further incremental rotation of the arm before application of the static and oscillatory forces (F) until the optimum location for data collection is passed by. When the optimum location for data collection is passed by, the measure of conformity will worsen. The optimized parameter set with respect to incremental rotation of the arm is represented by the best measure of conformity of the saved parameter sets.

The optimized parameter set may further be determined based on shifting the region for the superposition of static and oscillatory forces (F) after determining the optimal rotational position of the arm. For example, the superposition of static and oscillatory forces (F) over a range of frequencies (f) may be initially applied to a region of the skin-bone complex medial of the centerline of the ulna, then the static and oscillatory forces (F) over a range of frequencies (f) are applied to a shifted region lateral of the initial region of the skin-bone complex, then the static and oscillatory forces (F) over a range of frequencies (f) are applied to a further shifted region further lateral of the initial region of the skin-bone complex. The measure of conformity improves upon each further lateral shift of the application of the static and oscillatory forces (F) until the optimum location for data collection is passed by. When the optimum location for data collection is passed by, the measure of conformity will worsen. The optimized parameter set with respect to medial to lateral shifting of the region is represented by the best measure of conformity of the saved parameter sets. Analogously, the region may be shifted longitudinally along the long axis of the forearm and an optimized parameter set with respect to longitudinal shifting of the region may be obtained. Furthermore, the magnitude of the static load, and thereby the position of the resonance determined primarily by the mechanical properties of the skin and soft tissues, may be varied and an optimized parameter set with respect to static load obtained. In addition, layers of viscoelastic material may be inserted between the skin and the force probe that applies force to the skin, and an optimized parameter set with respect to the number of layers obtained. In this way an overall optimized parameter set is identified.

Upon determination of the overall optimized parameter set, the stiffness of the bone can be determined. Additionally, in various embodiments, each of the individual optimized parameter sets may be used to determine the stiffness of the bone. Transverse bending stiffness of the bone ($K_B$) can be determined directly from the parametric parameters associated with the optimized parameter set. In embodiments, the determined stiffness of the bone is the transverse bending stiffness of the bone ($K_B$) generated from Y(f) as part of the first complete and fully converged set of parameters associated with the optimized parameter set. In other embodiments, the determined stiffness of the bone is the transverse bending stiffness of the bone ($K_B$) generated from H(f) as part of the second complete and fully converged set of parameters associated with the optimized parameter set. In still other embodiments, the determined stiffness of the bone is an average of the transverse bending stiffness of the bone ($K_B$) generated from Y(f) as part of the first complete and fully converged set of parameters associated with the optimized parameter set and the transverse bending stiffness of the bone ($K_B$) generated from H(f) as part of the second complete and fully converged set of parameters associated with the optimized parameter set. In yet still other embodiments, the determined stiffness of the bone is a weighted average of the transverse bending stiffness of the bone ($K_B$) generated from Y(f) as part of the first complete and fully converged set of parameters associated with the optimized parameter set and the transverse bending stiffness of the bone ($K_B$) generated from H(f) as part of the second complete and fully converged set of parameters associated with the optimized parameter set.

Additionally, in multiple embodiments, the determined stiffness of bone in the method is flexural rigidity, EI, and may be calculated based on the determined transverse bending stiffness 6 ($K_B$) of the bone. Specifically, $EI=K_B L^3/48$, wherein L is the length of the bone.

In various embodiments, the measure of conformity between the first complete and fully converged set of parameters and the second complete and fully converged set of parameters is quantified as a root mean square (RMS) therebetween of the percentage differences between the seven parameters estimated from Y(f) and H(f), i.e. percentage root mean square (% RMS).

Additionally, in accordance with the 7-parameter model, each of the parameters must have a positive value in the optimized parameter set. Specifically, mass of the skin 8 ($M_S$), transverse bending stiffness of the skin 2 ($K_S$), damping coefficient of the skin 12 ($B_S$), mass of the bone 10 ($M_B$), transverse bending stiffness of the bone 6 ($K_B$), damping coefficient of the bone 14 ($B_B$), and damping coefficient of the surrounding soft tissue 4 ($B_P$) are all by definition positive values. Thus, in embodiments, if the first complete and fully converged set of parameters or the second complete and fully converged set of parameters include a negative parameter value it is known that the sets of parameters are not ideal and thus do not represent the optimized parameter set.

Further, with reference to FIG. 3, the area under the imaginary part of the compliance curve between 40 Hz and 100 Hz is preferably less than $6\times10^{-4}$ m/Ns. In the 7-parameter model, the imaginary part of compliance approaches zero as frequency approaches zero. If the sub-range of frequency that minimizes % RMS does not include frequencies below 100 Hz, then departure from this feature of the 7-parameter model will not be detected by % RMS alone. Therefore, for greater confidence in conformity to the 7-parameter model, the area under the imaginary part of the compliance curve between 40 Hz and 100 Hz should be substantially less than approximately $6\times10^{-4}$ m/Ns=$1\times10^{-5}$ m/N×60 Hz. If the imaginary part of compliance does not approach zero as frequency approaches zero the collected data is believed to be suboptimal.

In further embodiments, the oscillatory forces (F) are applied to the skin-bone complex through an excitation frequency range. In embodiments, the excitation frequency range has a minimum frequency of approximately 40 Hz and a maximum frequency of approximately 1200 Hz. In further embodiments, the excitation frequency range has a minimum frequency of approximately 80 Hz and a maximum frequency of approximately 1100 Hz. In still further embodiments, the excitation frequency range has a minimum frequency of approximately 100 Hz and a maximum frequency of approximately 1000 Hz.

In various embodiments, the excitation frequency range is selected such that the lower end or minimum frequency of the excitation frequency range is substantially less than the frequency of the bone peak 20 resonance frequency in the imaginary part 24 of the compliance frequency response function, and the upper end or maximum frequency of the excitation frequency range is substantially above the frequency of the skin peak 22 resonance frequency in the imaginary part 24 of the compliance frequency response function.

In various embodiments, the oscillatory forces (F) are applied over the excitation frequency range in a swept sine waveform, a pseudorandom waveform, a shaped random waveform, a chirp waveform, a burst waveform, a burst random waveform, a shaped burst random waveform, a white noise waveform, a pink noise waveform, or other standard waveforms known to one of ordinary skill in the art.

In various embodiments, the parametric mathematical model is fit to Y(f) and H(f) at a plurality of subranges within the excitation frequency range. In theory, for data conforming perfectly to the 7-parameter model, fitting the 7-parameter model to either Y(f) or H(f) should yield exactly the same estimates of the 7 parameters regardless of the frequency range over which the model is fitted; however, in practice it does not. Fitting the parametric mathematical model at a plurality of subranges produces a plurality of first and second sets of parameters and thus the subrange with the best measure of conformity for the first and second complete and fully converged set of parameters may be selected. Specifically, in embodiments, the controller fits the 7-parameter model to both Y(f) and H(f) over a large number of frequency subranges with varying low starting frequencies, i.e., minimum frequencies, and varying high ending frequencies, i.e., maximum frequencies. Fitting the 7-parameter model to both Y(f) and H(f) produces a plurality of first and second sets of parameters. The controller then instructs the processor to calculate the percentage root mean square of the differences between the first and second sets of parameters for each frequency subrange and reports the minimum percentage root mean square as a measure of the extent to which A(f) departs from the form of the 7-parameter model. It will be appreciated that 10s, 100s, or 1000s of individual measurements at distinct frequency ranges are completed to select the single measurement with the minimum percentage root mean square as the final reported first complete and fully converged set of parameters and second complete and fully converged set of parameters.

In further embodiments, the plurality of subranges within the excitation frequency range are generated by increasing the minimum frequency in repeated intervals and reducing the maximum frequency in repeated intervals. For example, in some embodiments, the minimum frequency is increased in approximately 5 Hz intervals and the maximum frequency is reduced in approximately 25 Hz intervals. With a excitation frequency range of approximately 40 Hz to approximately 1200 Hz a non-exhaustive listing of approximations of the subranges includes 45 Hz to 1200 Hz, 50 Hz to 1200 Hz, 55 Hz to 1200 Hz, 60 Hz to 1200 Hz, 65 Hz to 1200 Hz, 70 Hz to 1200 Hz, 40 Hz to 1175 Hz, 40 Hz to 1150 Hz, 40 Hz to 1125 Hz, 40 Hz to 1100 Hz, 40 Hz to 1075 Hz, 45 Hz to 1175 Hz, 45 Hz to 1150 Hz, 45 Hz to 1125 Hz, 45 Hz to 1100 Hz, 50 Hz to 1175 Hz, 50 Hz to 1150 Hz, 50 Hz to 1125 Hz, 50 Hz to 1100 Hz, and 50 Hz to 1075 Hz.

In further embodiments, various repeated intervals of increase for the minimum frequency ranging from approximately 1 Hz to approximately 20 Hz are envisioned and various repeated intervals of reduction for the maximum frequency ranging from approximately 5 Hz to approximately 50 Hz are envisioned with all permutations thereof specifically envisioned. For example, in some embodiments, the minimum frequency is increased in approximately 1 Hz intervals and the maximum frequency is reduced in approximately 5 Hz intervals, alternatively, the minimum frequency is increased in approximately 3 Hz intervals and the maximum frequency is reduced in approximately 10 Hz intervals, alternatively, the minimum frequency is increased in approximately 10 Hz intervals and the maximum frequency is reduced in approximately 20 Hz intervals, alternatively, the minimum frequency is increased in approximately 10 Hz intervals and the maximum frequency is reduced in approximately 30 Hz intervals, alternatively, the minimum frequency is increased in approximately 5 Hz intervals and the maximum frequency is reduced in approximately 20 Hz intervals, alternatively, the minimum frequency is increased in approximately 20 Hz intervals and the maximum frequency is reduced in approximately 50 Hz intervals.

In various embodiments, the minimum frequency is increased in repeated intervals until reaching a threshold minimum frequency. Similarly, the maximum frequency is reduced in repeated intervals until reaching a threshold maximum frequency. For example, in an embodiment, the minimum frequency is increased in approximately 5 Hz intervals until reaching a threshold minimum frequency of approximately 180 Hz and the maximum frequency is reduced in approximately 25 Hz intervals until reaching a threshold maximum frequency of approximately 700 Hz. In other embodiments, the threshold minimum frequency is 120, 140, 160, 180, or 200 and the threshold maximum frequency is 650, 700, 750, 800, or 850 with each combination thereof specifically envisioned. The threshold minimum and threshold maximum frequencies ensure that the plurality of subranges generated in the excitation frequency range all include the range between the threshold minimum frequency and the threshold maximum frequency as the minimum frequency is never higher than the threshold minimum frequency nor lower than the threshold maximum frequency. With reference to FIGS. 2 and 3, the threshold minimum and threshold maximum frequencies are selected such that the bone peak 20 of Y(f) and the skin peak 22 of Y(f) are contained within the frequency range enclosed by the threshold minimum frequency and the threshold maximum frequency. Typically, the bone peak 20 of Y(f) is centered at approximately 150-250 Hz and the skin peak of Y(f) is centered at approximately 500-800 Hz. In a further embodiment, the threshold minimum frequency is selected as the resonant frequency representing the bone peak and the threshold maximum frequency is selected as the resonant frequency representing the skin peak.

In various embodiments, each determination of the stiffness of the bone requires approximately 1 minute. Specifically, applying the superposition of static and oscillatory forces (F) over a range of frequencies (f) to a region of the skin-bone complex, receiving the oscillatory forces as functions of time F(t) and oscillatory accelerations as functions of time a(t), and the subsequent fitting of the parametric mathematical model to Y(f) and H(f) takes about 1 minute. The static and oscillatory forces (F) are then applied to the shifted region and a revised stiffness of bone is generated along with a revised measure of conformity; this measurement and analysis also requires approximately 1 minute. Typically, in some embodiments, approximately 15 parameter sets are obtained before the optimized parameter set is determined yielding an elapsed testing time of approximately 15 minutes for the patient. It will be appreciated that determination of each parameter set includes 10s, 100s, or 1000s of individual measurements.

The optimized parameter set represents the parameter set which is believed to most closely reflect a true and accurate parameter set. The optimized parameter set may be determined by selecting the parameter set having the minimum percentage root mean square of the entirety of the parameter sets obtained from all the tested skin-bone complex locations and rotational positions. Such may be determined based on the measure of conformity. As such, a first complete and fully converged set of parameters and a second complete and fully converged set of parameters are obtained from 100s, 1000s, or 10,000s of measurements at differing locations, rotational positions, and frequency ranges with the optimized parameter set representing the specific measurement which produced the minimum percentage root mean square as evidenced by the measure of conformity obtained in each measurement cycle. It will be appreciated that the optimized parameter set may additionally represent an average or other weighting protocol of a set of the parameter sets representing those with the 2, 3, 4, 5, 10, or 25 lowest percentage root mean squares.

Figure 8:
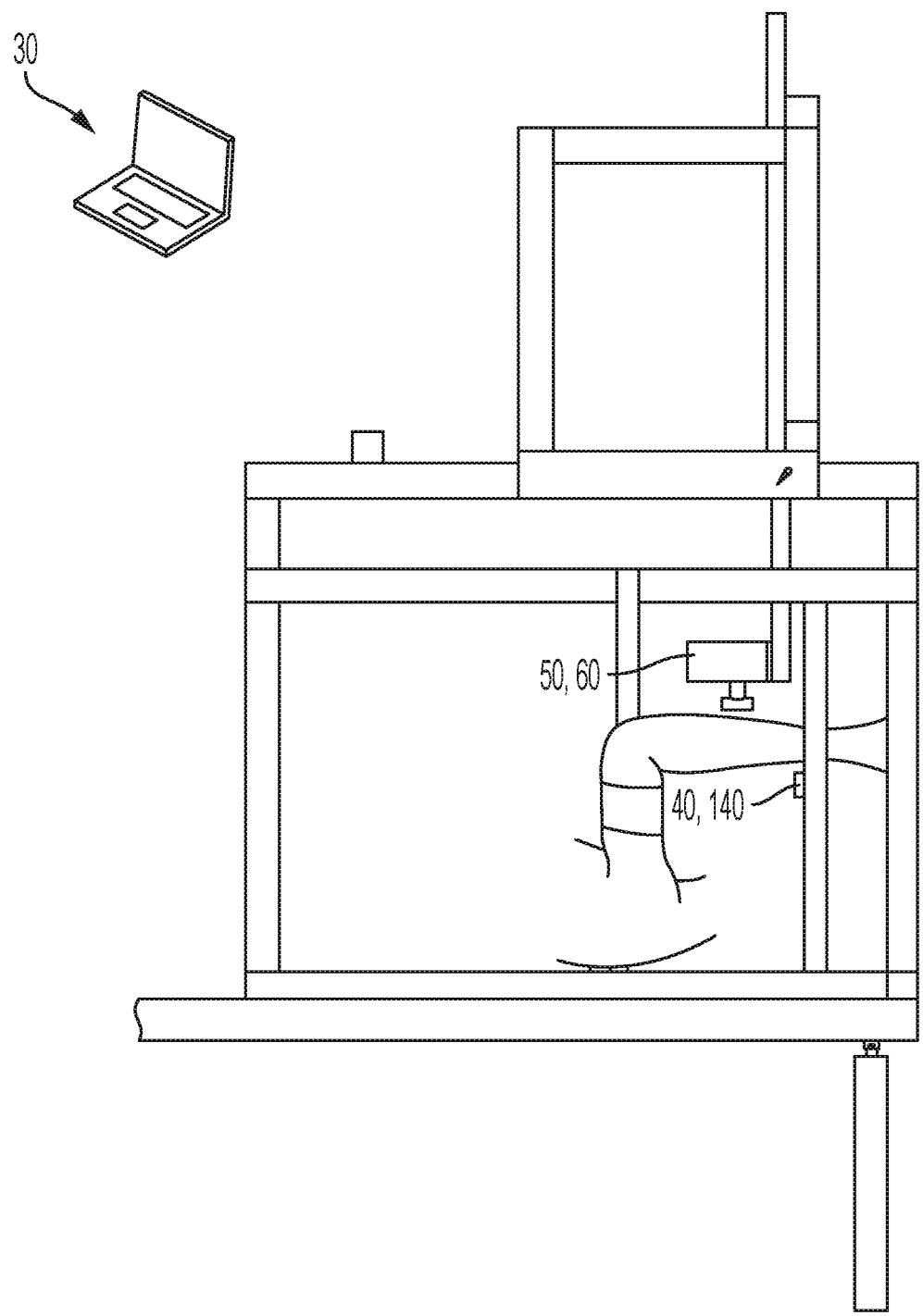
FIG. 8 depicts a side view of a system for estimating the stiffness of a bone in vivo according to at least one embodiment.
Figure 9:
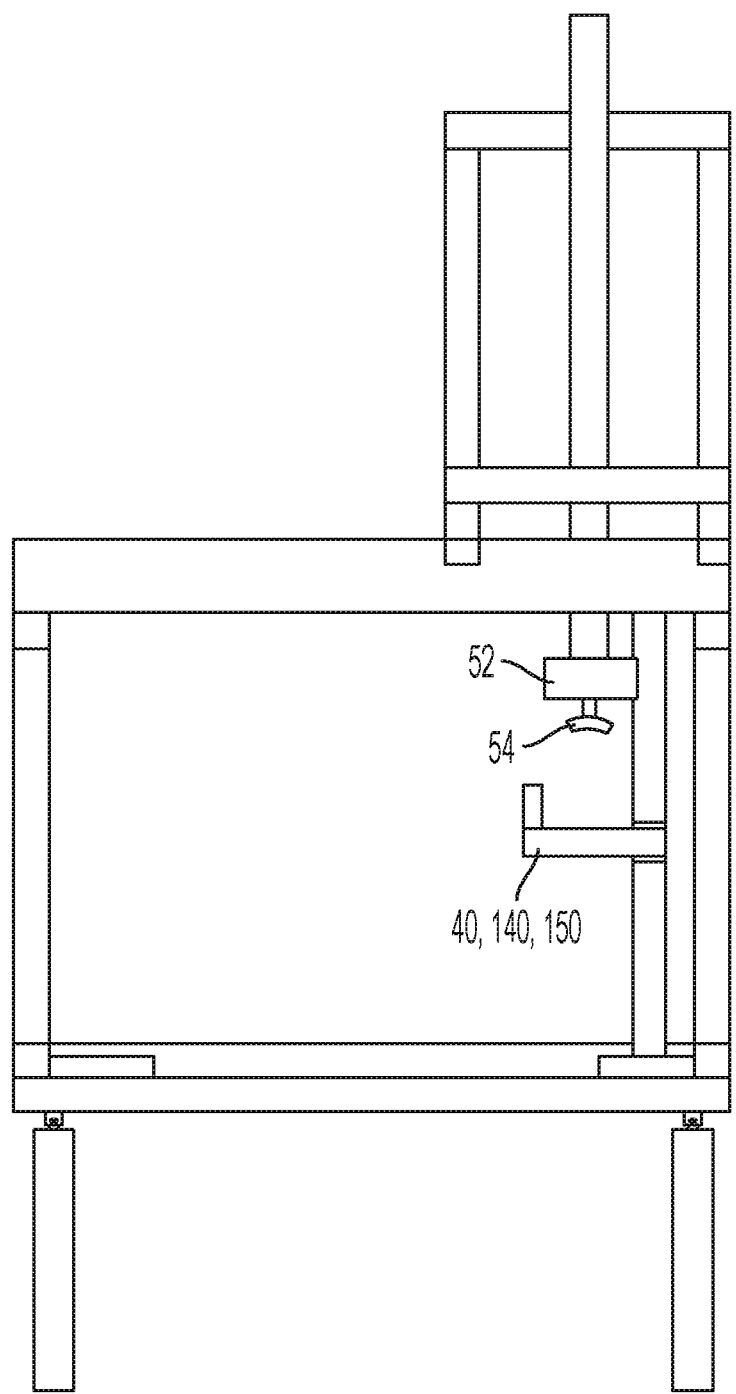
FIG. 9 depicts a front view of a system for estimating the stiffness of a bone in vivo according to at least one embodiment.

Referring to FIGS. 8 and 9, in further embodiments, a system for estimating the stiffness of an ulna bone in vivo is provided. The system includes a device for measuring the stiffness of the ulna bone in vivo as well as a data analyzer 30. In various embodiments the device for measuring the stiffness of the ulna bone in vivo includes a bone positioning support 40, a mechanical force applicator 50, and a frequency response recorder 60. The bone positioning support 40 is configured to position and support an arm comprising the ulna bone and a radius bone in an orientation and position for measurement. The mechanical force applicator 50 includes a force transducer 52 and a force probe 54 and is configured to apply static and oscillatory forces (F) to a region of the skin-bone complex comprising the ulna, the radius, and the overlying muscle and skin. The static and oscillatory forces (F) applied to the skin-bone complex by the mechanical force applicator 50 include oscillatory forces (F) which in turn create oscillatory accelerations (a) of the skin-bone complex. Finally, the frequency response recorder 60 is configured to measure and transmit to the data analyzer 30, e.g. a computer, the oscillatory forces (F) and the oscillatory accelerations (a).

With reference to FIG. 9, in various embodiments, the mechanical force applicator 50 comprises a force transducer 52 and a force probe 54. The force transducer 52 provides the static and oscillatory forces via the force probe 54. The force transducer 52 provides the oscillatory forces (F) when driven by an oscillatory electrical control signal and the static force when driven by a constant electrical control signal to the force probe 54. In further embodiments, the force transducer 52 provides the oscillatory forces (F) to the force probe 54 and the static force is provided by manually or electromechanically moving the force applicator 50 to a desired position. The mechanical force applicator 50 is controllably positionable to permit the position of the mechanical force applicator 50 to be controllably adjusted in three orthogonal dimensions, relative to patient's arm and the underlying ulna bone.

In various embodiments of a system for estimating the stiffness of an ulna bone in vivo, the data analyzer 30 is communicatively coupled to the force transducer 52 and frequency response recorder 60 and the data analyzer 30 includes a storage medium and a processor. The storage medium contains computer readable and executable instructions for collecting the transmitted oscillatory forces as functions of time F(t) and oscillatory accelerations as functions of time a(t) of the skin-bone complex from the frequency response recorder. Additionally, the storage medium stores a parametric model of the skin-bone complex, such as was previously discussed above. The processor is provided for executing the instructions to transform a(t) and F(t) to functions of frequency, a(f) and F(f). The processor is also provided for executing the instructions to reduce a(f) and F(f) to acceleration frequency response data A(f) such as previously discussed. Further, the processor is provided for executing the instructions to determine a complex compliance frequency response function Y(f) and associated complex stiffness frequency response function H(f), to fit the parametric mathematical model to Y(f) to obtain a first complete and fully converged set of parameters of the parametric mathematical model, including the stiffness of the bone ($K_B$), and to fit the parametric mathematical model to H(f) to obtain a second complete and fully converged set of parameters of the parametric mathematical model, including the stiffness of the bone ($K_B$), such as previously discussed. Further, the processor determines the discrepancies between the first complete and fully converged set of parameters and the second complete and fully converged set of parameters as a measure of conformity thereof to the parametric mathematical model, such as previously discussed above.

In further embodiments of a system for estimating the stiffness of an ulna bone in vivo, the data analyzer 30 is connected to a visual subsystem with a graphical user interface (GUI). The visual subsystem and graphical user interface provides information to the technician and/or operator of the system. In various embodiments, the information provided to the technician and/or operator includes displays of the fit of the parametric mathematical model to the accelerance frequency response function data A(f), the complex compliance frequency response function Y(f), and/or the complex stiffness frequency response function H(F). For example, graphical display of a curve representing experimental Y(f), H(f), and/or A(f) may be displayed with a curve generated by the best fit parameters overlaid in each instance. Additionally, statistical indicators of the fit of the parametric mathematical model to the accelerance frequency response function data A(f), the complex compliance frequency response function Y(f), and/or the complex stiffness frequency response function H(F) may be provided, such as in tabular form. For example, $R^2$ may be provided to indicate the goodness of the best fit parameters to the complex compliance frequency response function Y(f) and/or the complex stiffness frequency response function H(F).

Further configurations and details of a generalized MRTA system are provided in United States Patent Application Publication US 2016/0058365, published Mar. 3, 2016 and incorporated herein by reference in its entirety.

In testing, MRTA and improved CBMT data are collected from a human subject lying prone upon a table. The arm of the patient is raised such that the upper arm including the humerus bone is vertical and the forearm including the radius and ulna is horizontal with the hand beside the head. As such, adjustability and positioning of the MRTA and improved CBMT testing system is undertaken to ensure proper support, positioning, and alignment of the various bones.

Figure 10A:
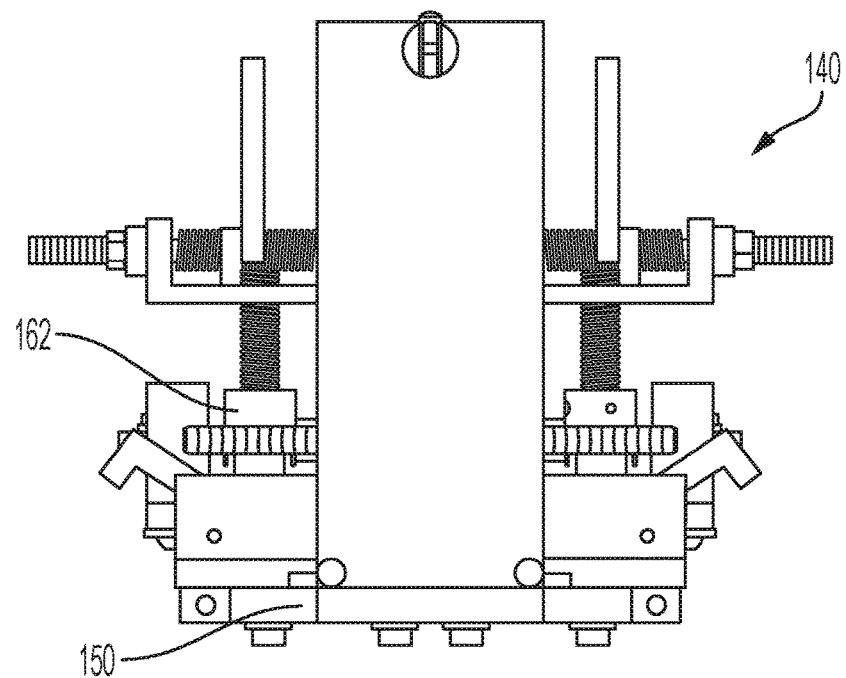
FIG. 10A depicts an end view of a bone support to position and support an arm in an orientation and position for measurement according to embodiments of the present disclosure.
Figure 10B:
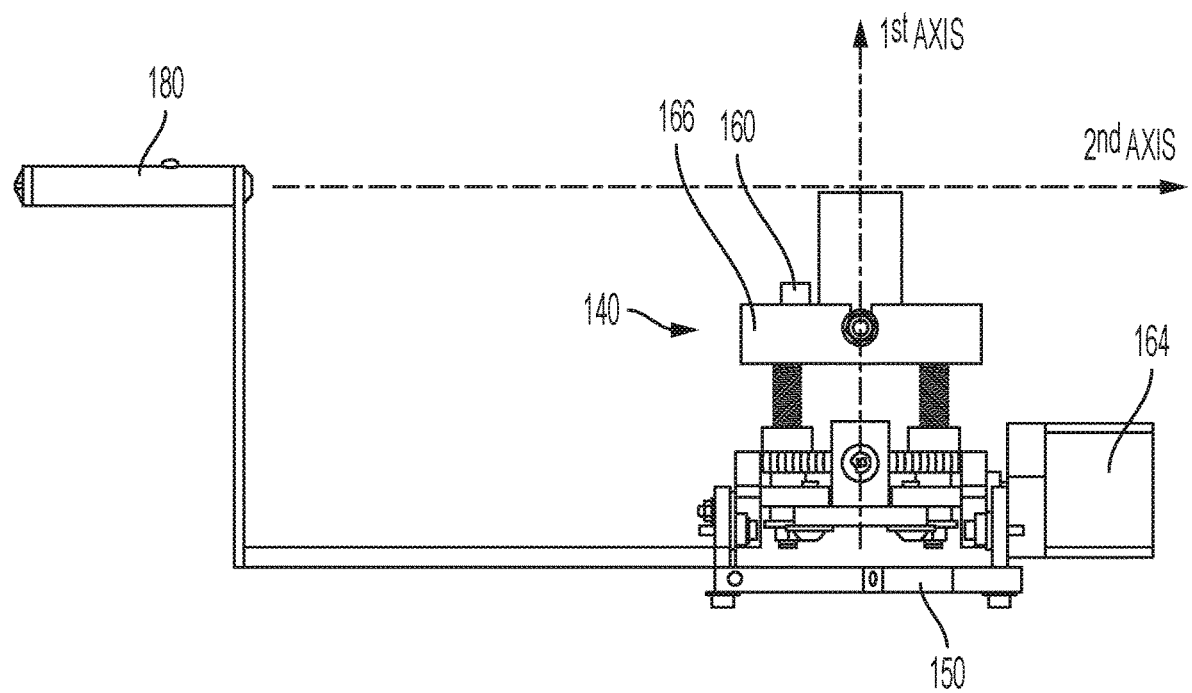
FIG. 10B depicts a side view of a bone support to position and support an arm in an orientation and position for measurement according to embodiments of the present disclosure.
Figure 10C:
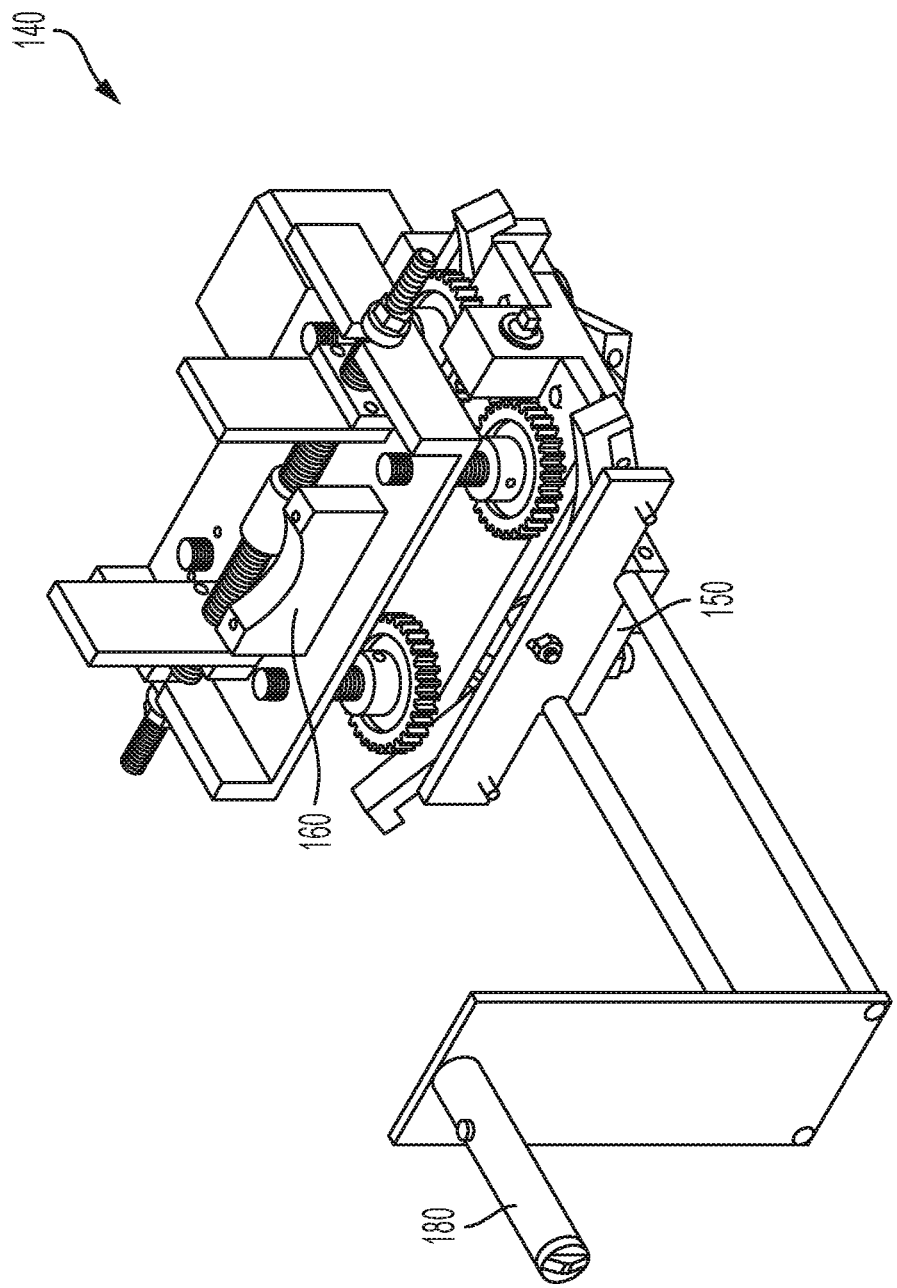
FIG. 10C depicts an oblique view of a bone support to position and support an arm in an orientation and position for measurement according to embodiments of the present disclosure.

With reference to FIGS. 10A, 10B, and 10C, in embodiments, the device for measuring the stiffness of the ulna bone in vivo includes a bone support which, in part, includes a cradle 140 to support the wrist. The cradle 140 provides controllable positioning and rotation of the arm with the styloid process of the radius bone resting on the cradle 140.

In various embodiments, the cradle 140 is affixed to a mount 150, the mount 150 adjustably positionable along an x-axis, a y-axis, and a z-axis. The adjustably positionable mount 150 permits the position of the arm to be controllably adjusted in three orthogonal dimensions, relative to the mechanical force applicator 50. The x, y, z control of the mount 150 provides substantial flexibility in positioning the arm with respect to the mechanical force applicator 50. The adjustment along the z-axis, commonly references as vertical, adjusts the arm to level the ulna bone with the humerus in a stationary position. The adjustment along the x-axis, which corresponds with a line horizontally parallel to the long axis of the patient's body, adjusts the arm to bring the elbow directly above the long axis of the humerus. Finally, the adjustment along the y-axis, which corresponds with a line transversely across the patient's body, adjusts the arm to bring the long axis of the humerus bone into orthogonality with the XY plane.

In embodiments, the cradle 140 comprises a saddle 160 for supporting the radius bone. The saddle 160 may comprise geometry to conform to the external topography of the distal portion of a human forearm. Specifically, the saddle 160 may comprise an arced profile to conform to the corresponding arc of a human forearm in the region of the styloid process of the radius bone. Additionally, the saddle 160 positions the longitudinal axis of the ulna bone in a known position relative to the cradle 140.

In one or more embodiments, the saddle 160 is adjustably positionable relative to the mount 150. The adjustability of the mount 150 provides course positioning of the distal forearm. The adjustability of the saddle 160 relative to the mount 150 provides fine positioning of the distal forearm. The adjustability of the saddle 160 relative to the mount 150 also provides adjustment of the distal forearm beyond translation along the three Cartesian axes (x, y, and z-axes) by allowing rotation about one or more of the axes.

Figure 11A:
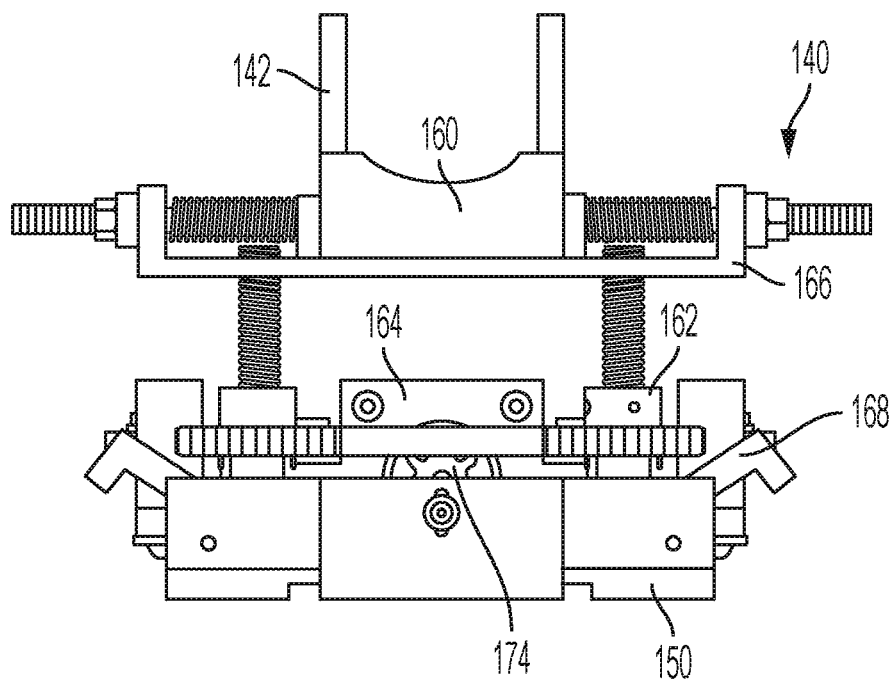
FIG. 11A depicts an end view of a bone support with the saddle in an elevated position according to embodiments of the present disclosure.
Figure 11B:
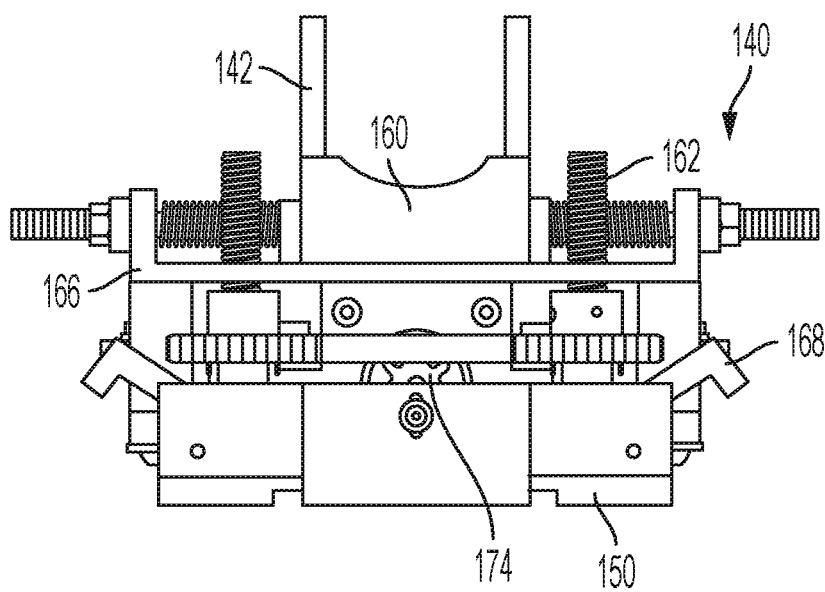
FIG. 11B depicts an end view of a bone support with the saddle in a retracted position according to embodiments of the present disclosure.

With reference to FIGS. 11A and 11B, in embodiments, the saddle 160 is controllably adjustable to positions more proximal and more distal the mount 150 along a first axis. With reference to FIG. 10B, the first axis may be visualized as spanning through the mount 150 and the saddle 160, an adjustment means, such as a worm gear 162 or hydraulic piston, may reposition the saddle 160 along the first axis. Repositioning the saddle 160 along the first axis results in the distance between the mount 150 and the saddle 160 increasing or decreasing depending on the direction of travel. With reference to FIG. 11A the saddle 160 is elevated and positioned relatively more distal from the mount 150 than in FIG. 11B where the saddle 160 is positioned more proximal to the mount 150. In various embodiments, the adjustment means may be driven manually or driven with a stepper motor 164, for example. The adjustment of the saddle 160 along the first axis raises and lowers the distal forearm to align the long axis of the ulna bone into the desired position and orientation.

Adjustment of the saddle 160 along the first axis is beneficial to allow for variance in the body size of patients. People differ greatly in body size, and consequentially also differ greatly in the distance from the base of support of the radius bone to the long axis of the ulna around which the radius rotates. With reference to FIGS. 5A and 5B and FIGS. 6A and 6B, the variability may be visualized. The arm displayed in FIGS. 5A and 5B has a lesser distance than the arm displayed in FIGS. 6A and 6B. Adjustment of the saddle 160 positioning provides for lowering the base of support in the form of the saddle 160 for the radius in FIGS. 6A and 6B or raising the base of support in the form of the saddle 160 in FIGS. 5A and 5B so that the long axis of the ulna is brought into congruity with the center of rotation of the radius around the ulna bone.

In embodiments, the saddle 160 is rotatably adjustable about a second axis perpendicular the first axis. With reference to FIG. 10B, the second axis may be visualized. In embodiments, the positioning of the saddle 160 along the first axis may be adjusted such that the second axis corresponds to a longitudinal axis of the ulna bone when the ulna bone is positioned in the saddle 160 of the cradle 140.

Figure 12A:
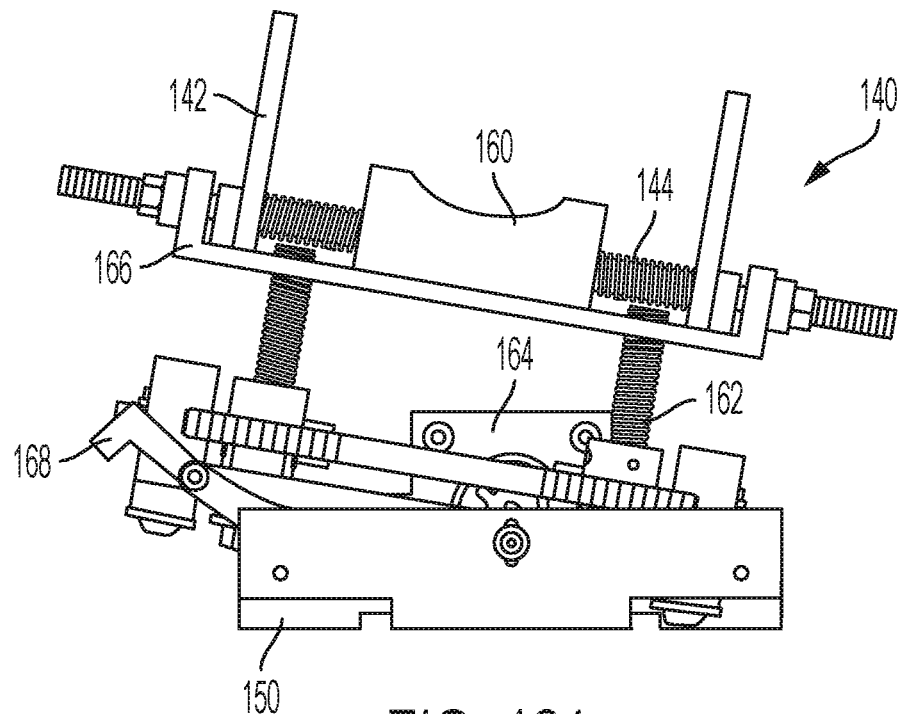
FIG. 12A depicts an end view of a bone support with the saddle rotated in a clockwise direction according to embodiments of the present disclosure.
Figure 12B:
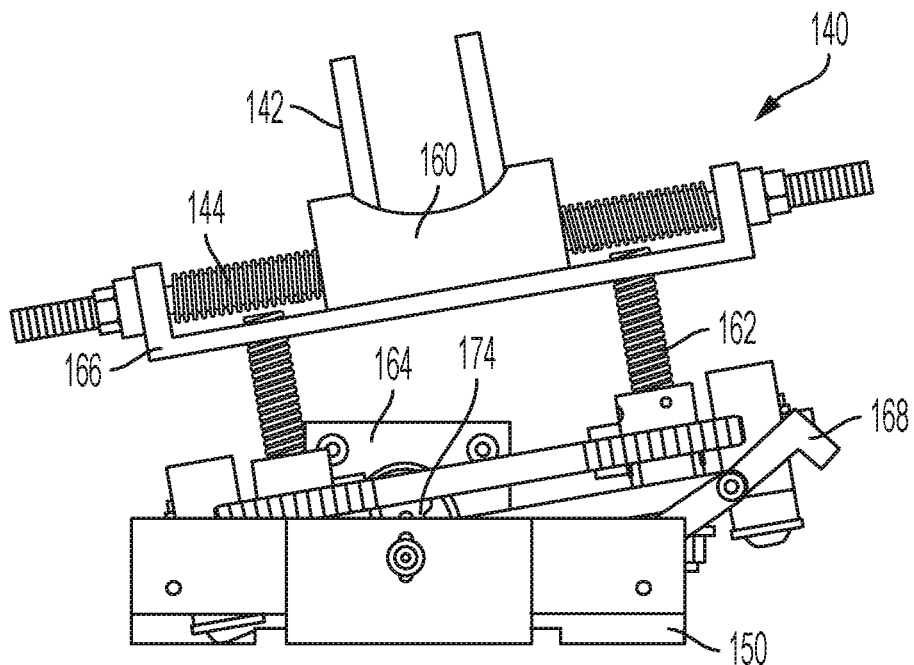
FIG. 12B depicts an end view of a bone support with the saddle rotated in a counter-clockwise direction according to embodiments of the present disclosure.

With reference to FIGS. 12A and 12B, in one or more embodiments, the saddle 160 is connected to a tilting platform 166 which pivots about the second axis. Specifically, tracks 168 with a circular arc geometry having a center of the arc corresponding to the second axis are provided in connection with the saddle 160 and the associated adjustment means for repositioning the saddle 160 along the first axis. The tracks 168 may be controllably rotated to adjust the saddle 160, which is attached to the tracks 168 via the adjustment means for repositioning the saddle 160 along the first axis, about the second axis. In one or more embodiments, one of the tracks 168 includes a curved rack 172 for engagement with a pinion gear 174 on a stepper motor 164 to controllably rotate the tracks 168. It may be seen in FIG. 12A the saddle 160 rotated in a clockwise direction around the second axis and in FIG. 12B the saddle 160 rotated in a counter-clockwise direction around the second axis.

The forces applied to the ulna bone during MRTA and improved CBMT testing are transmitted from the ulna bone, through the distal radius bone, through the saddle 160, the tilting platform 166, and into the mount 150.

In one or more embodiments, the cradle 140 may further comprise stabilizing jaws 142 to retain the forearm positioned in the saddle 160. The stabilizing jaws 142 may be connected to the saddle 160, the cradle 140, or both With reference to FIGS. 12A and 12B, the stabilizing jaws 142 comprise two or more adjustable barriers which may be constricted to secure a human forearm positioned therein. FIG. 12A provides the stabilizing jaws 142 in an expanded configuration and FIG. 12B provides the stabilizing jaws 142 in a constricted configuration. In various embodiments, the relative proximity of the adjustable barriers of the stabilizing jaws 142 may be adjusted with one or more screws 144, pistons, or other means of displacement known to those having ordinary skill in the mechanical arts. In one or more embodiments, the adjustable barriers of the stabilizing jaws 142 may be rigid members in a planar or curvilinear configuration to provide non-compliant pressure to the forearm during securement. Exemplary stabilizing jaws 142 comprising rigid members may be comprised of stainless steel or rigid plastics. In further embodiments, the adjustable barriers of the stabilizing jaws 142 may be resilient members in a planar or curvilinear configuration to deform to the geometry of the forearm and provide compliant pressure to the forearm during securement. Exemplary stabilizing jaws 142 comprising resilient members may be comprised of closed cell foams or rubbers.

Figure 13:
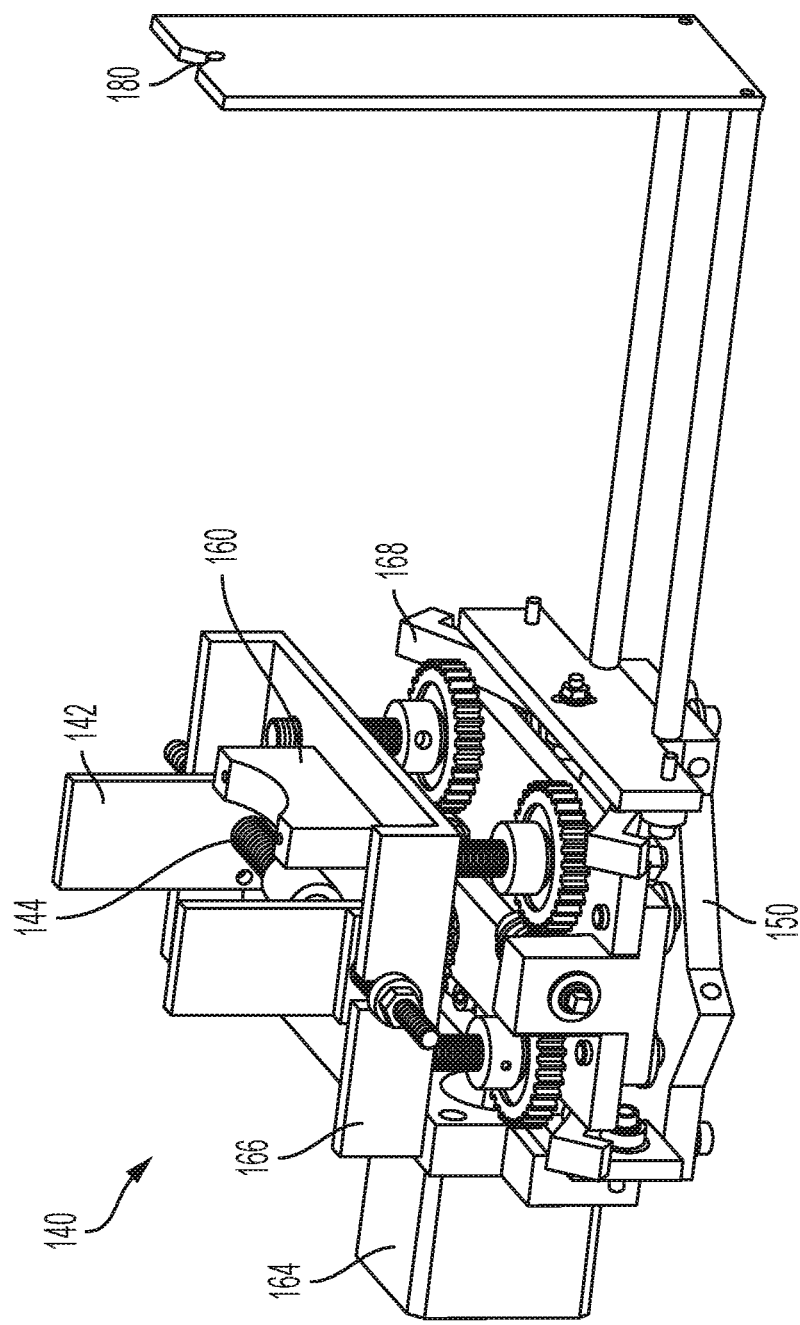
FIG. 13 depicts an oblique view of a bone support according to embodiments of the present disclosure.

In one or more embodiments, the cradle 140 or mount 150 comprises a positioning indices 180 for indicating the location of the second axis. Specifically, as the second axis corresponds to the center of the arc of the tracks 168, the second axis is at a known position relative to the cradle 140 and mount 150. In embodiments, the positioning indices 180 comprises a sighting mechanism in alignment with the length of the second axis. With reference to FIGS. 10B and 10C, the positioning indices 180 may comprise a laser in alignment with the second axis. In further embodiments, with reference to FIG. 13, the positioning indices 180 may comprise a hole, notch, peep sight or other indices which may be used as a sighting mechanism to indicate the position of the second axis. The positioning indices 180 allows the operator during MRTA and improved CBMT testing to align the longitudinal axis of the ulna with the second axis. The location of the distal end of the ulna may be determined with external examination by palpation for the styloid process allowing the operator to adjust the positioning of the saddle 160 such that the distal end of the ulna on the saddle 160 is in alignment with the second axis.

Figure 14:
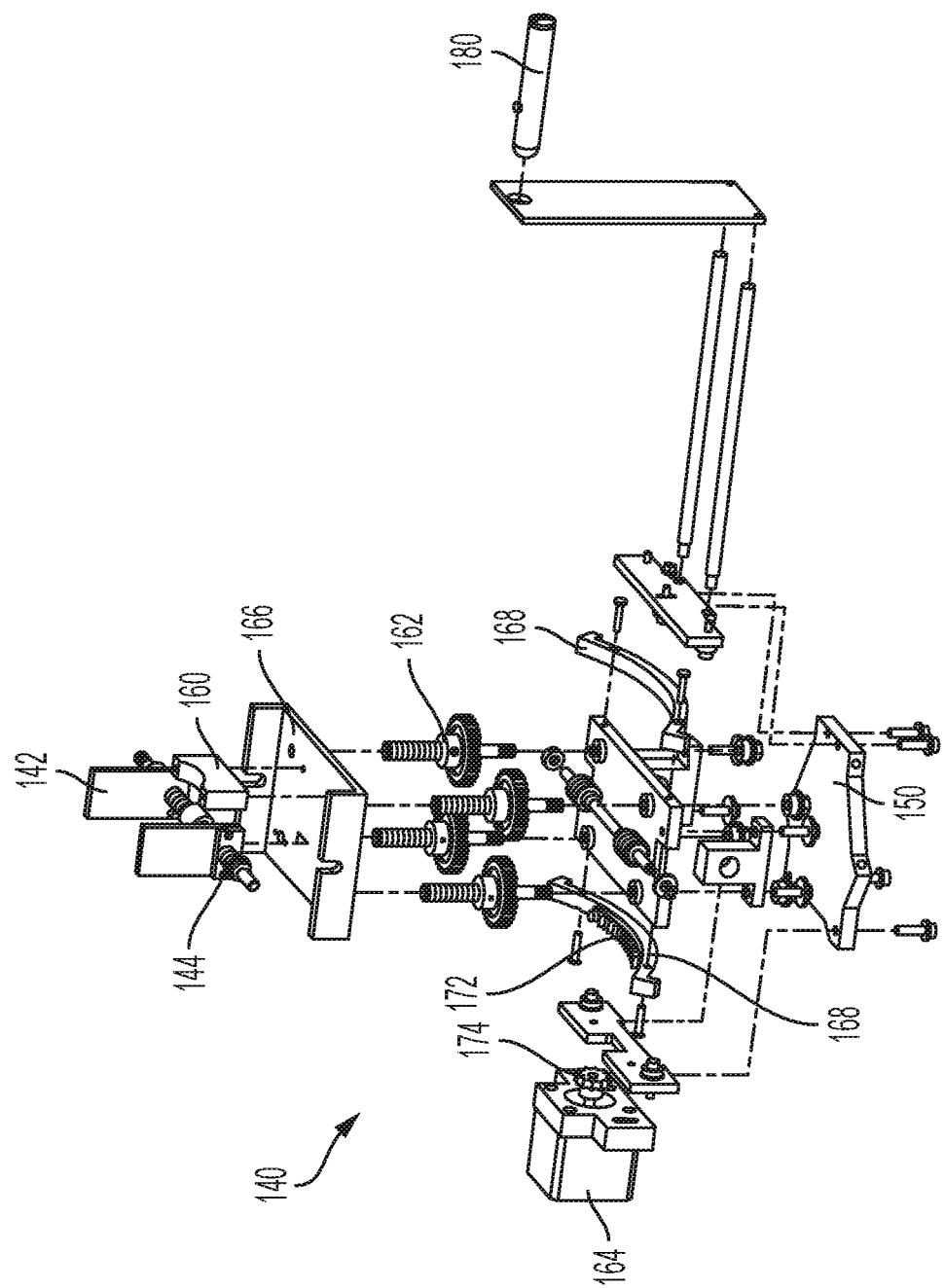
FIG. 14 depicts an exploded view of a bone support according to embodiments of the present disclosure.

With reference to FIG. 14, an exploded view of an embodiment of the cradle 140, mount 150, and saddle 160 is provided.

It should now be understood that various aspects of the disclosed method and system are described herein and that such aspects may be utilized in conjunction with various other aspects.

Having shown and described various embodiments in the present disclosure, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometries, materials, dimensions, ratios, steps, and the like discussed above are illustrative and are not required. Accordingly, the scope of the present invention should be considered in terms of the following claims and understood not to be limited to the details of structure and operation shown and described in the specification and drawings.

As will be evident from the foregoing disclosure, the methods of the invention are carried out non-invasively. As will be evident from the foregoing disclosure, the methods of the invention are carried out non-invasively. Additionally, the methods of the invention can be carried out by technicians without medical training and in the absence of medical supervision.

The invention claimed is:

1. A parametric model based computer implemented method for determining the stiffness of a human ulna bone, comprising:
    (1) supporting an arm comprising the ulna bone and a radius bone on a cradle comprising a saddle for supporting the ulna bone, the cradle providing controllable positioning and rotation of the arm with the styloid process of the radius bone resting on the cradle;
    (2) applying a superposition of static and oscillatory forces (F) over a range of frequencies (f) to a region of a skin-bone complex comprising the ulna, the radius, and the overlying muscle and skin thereby exciting oscillatory accelerations (a) over the range of frequencies (f) of the skin-bone complex;

(3) receiving measurement data of the oscillatory forces (F) as functions of time F(t) and obtaining the resulting oscillatory acceleration data (a) as functions of time a(t) with a data receiver communicatively coupled to a controller comprising a processor and a storage medium containing computer readable and executable instructions which, when executed by the processor, cause the controller to automatically:

(i) transform a(t) and F(t) to functions of frequency, a(f) and F(f), (ii) reduce a(f) and F(f) to accelerance frequency response function data A(f), (iii) determine, a complex compliance frequency response function, Y(f) and associated complex stiffness frequency response function H(f), (iv) fit a parametric mathematical model to the complex compliance frequency response function Y(f), by iteratively convergent operations, to obtain a first complete and fully converged set of parameters of the parametric mathematical model, including the stiffness of the bone ($K_B$), (v) independently fit the parametric mathematical model to the complex stiffness frequency response function H(f), by iteratively convergent operations, to obtain a second complete and fully converged set of parameters of the parametric mathematical model, including the stiffness of the bone ($K_B$), (vi) after fitting, determine discrepancies between each parameter of the first complete and fully converged set of parameters and each corresponding parameter of the second complete and fully converged set of parameters as a measure of conformity thereof to the parametric mathematical model, and (vii) save the measure of conformity, the first complete and fully converged set of parameters, and the second complete and fully converged set of parameters as a parameter set for the measured region of the skin-bone complex;

(4) adjusting a rotational position of the arm in the cradle such that a distal end of the radius bone is controllably rotated under the ulna bone;

(5) repeating step (2)-(4), such that the static and oscillatory forces (F) in step (2) are applied to a rotationally shifted region of the skin-bone complex, thereby obtaining a parameter set for the rotationally shifted region of the skin-bone complex;

(6) repeating step (5) until an optimized parameter set is determined based on the measure of conformity; and (7) determining the stiffness of the bone from ($K_B$) values of the optimized parameter set.

2. The method of claim 1, wherein the complex compliance frequency response function Y(f) is determined by integrating A(f) twice and wherein Y(f) is inverted to obtain the complex stiffness frequency response function H(f).

3. The method of claim 1, wherein the cradle is affixed to a mount, the mount adjustably positionable along a x-axis, a y-axis, and a z-axis.

4. The method of claim 1, wherein the cradle is affixed to a mount, the saddle adjustable positionable relative to the mount.

5. The method of claim 4, wherein the saddle is controllably adjustable to positions more proximal and more distal the mount along a first axis.

6. The method of claim 5, wherein the saddle is rotatably adjustable about a second axis perpendicular the first axis.

7. The method of claim 6, wherein the second axis corresponds to a longitudinal axis of the ulna bone when positioned in the saddle of the cradle.

8. The method of claim 1, wherein the measure of conformity between the first complete and fully converged set of parameters and the second complete and fully converged set of parameters is quantified in step (vi) as a root mean square therebetween of the percentage differences between each of the parameters of the first complete and fully converged set of parameters and the second complete and fully converged set of parameters.

9. The method of claim 1, wherein the oscillatory forces (F) are applied to the skin-bone complex through an excitation frequency range having a minimum frequency of approximately 40 Hz and a maximum frequency of approximately 1200 Hz:

the parametric mathematical model is fit to Y(f) and H(f) in steps (iv)-(v) at a plurality of subranges within the excitation frequency range;

a root mean square of the percentage differences between each of the parameters of the first complete and fully converged set of parameters and the second complete and fully converged set of parameters is quantified with the processor, for each of the plurality of subranges within the excitation frequency range; and a minimum resultant of the root mean square for the plurality of subranges is used as the measure of conformity in step (vi).

10. The method of claim 1, wherein the parametric mathematical model includes seven parameters comprising mass of the skin ($M_S$), transverse bending stiffness of the skin ($K_S$), damping coefficient of the skin ($B_S$) mass of the bone ($M_B$), transverse bending stiffness of the bone ($K_B$), damping coefficient of the bone ($B_B$), and damping coefficient of the surrounding soft tissue ($B_P$):

the parametric mathematical model is fit to Y(f) and H(f) in steps (iv)-(v) at a plurality of subranges within the excitation frequency range;

a root mean square of the percentage differences between each of the parameters of the first complete and fully converged set of parameters and the second complete and fully converged set of parameters is quantified with the processor, for each of the plurality of subranges within the excitation frequency range; and a minimum resultant of the root mean square for the plurality of subranges is used as the measure of conformity in step (vi).

11. The method of claim 1, wherein the stiffness of the bone from ($K_B$) values of the optimized parameter set is determined by selecting ($K_B$) from the first complete and fully converged set of parameters, ($K_B$) from the second complete and fully converged set of parameters, an average of ($K_B$) from the first complete and fully converged set of parameters and ($K_B$) from the second complete and fully converged set of parameters, or a weighted average of ($K_B$) from the first complete and fully converged set of parameters and ($K_B$) from the second complete and fully converged set of parameters of the optimized parameter set.

12. A system for estimating the stiffness of an ulna bone in vivo, the system comprising a device for measuring the stiffness of the ulna bone in vivo and a data analyzer:

the device for measuring the stiffness of the ulna bone in vivo comprising a bone support, a mechanical force applicator, and a frequency response recorder, wherein:

the bone support is configured to position and support an arm comprising the ulna bone and a radius bone in an orientation and position for measurement and comprises a cradle comprising a saddle for supporting the ulna bone, the cradle providing controllable positioning and rotation of the arm with the styloid process of the radius bone resting on the cradle;

the mechanical force applicator comprises a force transducer and a force probe and is configured to apply a superposition of static and oscillatory forces (F) over a range of frequencies (f) to a region of a skin-bone complex comprising the ulna, the radius, and the overlying muscle and skin, wherein the oscillatory forces (F) excite oscillatory accelerations (a) of the skin-bone complex; and the frequency response recorder is configured to measure and transmit to the data analyzer the oscillatory forces as functions of time F(t) and the oscillatory accelerations as functions of time a(t); and the data analyzer communicatively coupled to the force transducer and frequency response recorder and comprising:
  a storage medium containing computer readable and executable instructions for collecting the transmitted oscillatory forces as functions of time F(t) and oscillatory accelerations as functions of time a(t) of the skin-bone complex, the storage medium storing a parametric mathematical model of the skin-bone complex; and
  a processor for executing the instructions to transform a(t) and F(t) to functions of frequency, a(f) and F(f), to reduce a(f) and F(f) to accelerance frequency response data A(f), to determine a complex compliance frequency response function Y(f) and associated complex stiffness frequency response function H(f), to fit the parametric mathematical model to Y(f) to obtain a first complete and fully converged set of parameters of the parametric mathematical model, including the stiffness of the bone ($K_B$), to independently fit the parametric mathematical model to H(f) to obtain a second complete and fully converged set of parameters of the parametric mathematical model, including the stiffness of the bone ($K_B$), and to determine the discrepancies between the first complete and fully converged set of parameters and the second complete and fully converged set of parameters as a measure of conformity thereof to the parametric mathematical model.

13. The system of claim 12, wherein the complex compliance frequency response function Y(f) is determined by integrating A(f) twice and wherein Y(f) is inverted to obtain the complex stiffness frequency response function H(f).

14. The system of claim 12, wherein the cradle is affixed to a mount, the mount adjustably positionable along a x-axis, a y-axis, and a z-axis.

15. The system of claim 12, wherein the cradle is affixed to a mount, the saddle adjustable positionable relative to the mount.

16. The system of claim 15, wherein the saddle is controllably adjustable to positions more proximal and more distal the mount along a first axis.

17. The system of claim 16, wherein the saddle is rotatably adjustable about a second axis perpendicular the first axis.

18. The system of claim 17, wherein the second axis corresponds to a longitudinal axis of the ulna bone when the radius bone is positioned in the saddle of the cradle.

19. The system of claim 17, wherein the cradle or mount comprises a positioning indices for indicating the location of the second axis.

20. The system of claim 19, wherein the positioning indices comprises a sighting mechanism in alignment with the length of the second axis.

* * * * *